(12) United States Patent  
Sullivan et al.

(10) Patent No.: US 8,513,219 B2  
(45) Date of Patent: Aug. 20, 2013

(54) SUBSTITUTED PHOSPHONATES AND THEIR USE IN DECREASING AMYLOID AGGREGATES

(75) Inventors: Alice Sullivan, London (GB); Adina Michael-Titus, London (GB); Lesley Robson, London (GB)

(73) Assignee: Queen Mary & Westfield College, University of London, London (GB)

( * ) Notice: Subject to any disclaimer, the term of this patent is extended or adjusted under 35 U.S.C. 154(b) by 337 days.

(21) Appl. No.: 12/598,510

(22) PCT Filed: May 2, 2008

(86) PCT No.: PCT/GB2008/001540  
§ 371 (c)(1),  
(2), (4) Date: Apr. 13, 2010

(87) PCT Pub. No.: WO2008/135743  
PCT Pub. Date: Nov. 13, 2008

(65) Prior Publication Data  
US 2010/0204183 A1 Aug. 12, 2010

(30) Foreign Application Priority Data  
May 2, 2007 (GB) .................................. 0708507.9

(51) Int. Cl.  
*A61K 31/675* (2006.01)  
*C07F 9/6506* (2006.01)

(52) U.S. Cl.  
USPC ........................................... 514/80; 548/113

(58) Field of Classification Search  
USPC .......................................... 514/80; 548/113  
See application file for complete search history.

(56) References Cited

U.S. PATENT DOCUMENTS 5,453,517 A  9/1995  Kuhn et al.  
6,284,748 B1  9/2001  Dang et al.  
(Continued)

FOREIGN PATENT DOCUMENTS  
CN  1548444  11/2004  
JP  2003532656  2/2001  
(Continued)

OTHER PUBLICATIONS

Crofts et al. J. Am. Chem. Soc. 1953, 75, 5738-5740.*  
(Continued)

*Primary Examiner* — Rebecca Anderson  
*Assistant Examiner* — Matthew Coughlin  
(74) *Attorney, Agent, or Firm* — Pepper Hamilton, LLP

(57) ABSTRACT

The invention relates to novel and known substituted phosphonates for use in ameliorating amyloid aggregates, particularly for use in the treatment of Alzheimer's disease.

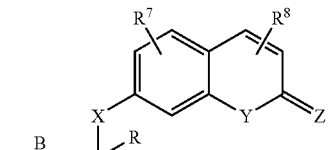

Ia

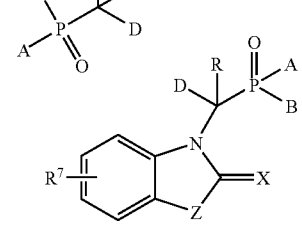

Ib

Ic

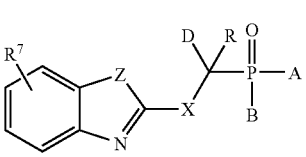

Id

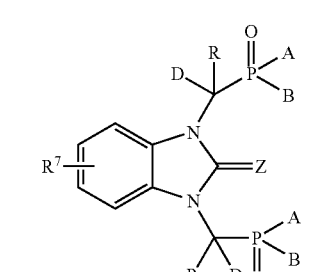

Ie

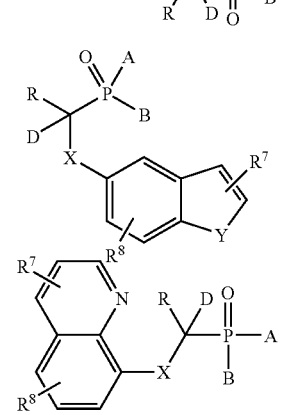

Ih

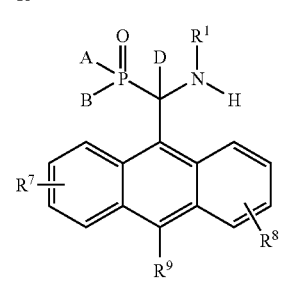

Ik

5 Claims, 17 Drawing Sheets

(56) References Cited

U.S. PATENT DOCUMENTS

| | | |
|---|---|---|
| 6,288,089 B1 | 9/2001 | Zawada et al. |
| 2002/0106354 A1 | 8/2002 | Anderson et al. |
| 2003/0013699 A1* | 1/2003 | Davis et al. .............. 514/210.02 |
| 2003/0225155 A1* | 12/2003 | Fernandez-Pol et al. ..... 514/448 |
| 2003/0236202 A1* | 12/2003 | Geelings et al. ................ 514/25 |
| 2004/0235751 A1* | 11/2004 | Frederickson ................ 514/18 |

FOREIGN PATENT DOCUMENTS

| | | |
|---|---|---|
| JP | 2001502681 | 11/2003 |
| WO | 98/17672 | 4/1998 |
| WO | 98/26773 A1 | 6/1998 |
| WO | 99/03878 | 1/1999 |
| WO | 99/58521 A1 | 11/1999 |
| WO | 00/43394 A | 7/2000 |
| WO | 01/51497 A1 | 7/2001 |
| WO | 01/85093 A1 | 11/2001 |
| WO | 02/38190 A2 | 5/2002 |
| WO | 02/097124 A1 | 12/2002 |
| WO | 03/059345 A1 | 7/2003 |
| WO | WO2004043394 | 5/2004 |
| WO | 2004/064728 A2 | 8/2004 |
| WO | 2004/087735 A2 | 10/2004 |
| WO | 2004/101579 A2 | 11/2004 |
| WO | WO2004101579 | 11/2004 |
| WO | WO 2004101579 A2 * | 11/2004 |
| WO | 2005/080406 A | 9/2005 |
| WO | WO2005080406 | 9/2005 |
| WO | 2006/050165 A2 | 5/2006 |
| WO | 2006/058411 | 6/2006 |
| WO | 2007/015122 A | 2/2007 |
| WO | 2007/017764 A2 | 2/2007 |
| WO | 2007/022059 | 2/2007 |
| WO | WO2007022059 | 2/2007 |
| WO | 2007/134449 | 11/2007 |

OTHER PUBLICATIONS

Arimilli, et al., 2003, CAS: 139:381609.
Erion, et al, 2000, CAS: 133:84284.
Dang, et al., 2000, CAS: 132:222529.
Van Poelje, et al., 2002, CAS: 136:123595.
Erion, et al., 2001, CAS: 135:348869.
Kasibhatla, et al., 1998, CAS: 129:245147.
He, et al., 1993, CAS: 119:203497.
Tanaka, et al., 1990, CAS: 112:108695.
Bartsch, et al., Selective transport of alkali metal cations in solvent extraction by proton-ionizable dibenzocrown ethers, Database Caplus, Chemical Abstracts Service, XP002310237 (1p.).
He, et al., Study on organophosphorus compounds with biological activity. Part III. Synthesis properties and biological activity of .alpha.-(benzothiazol-2-yl-oxy)alkanephosphonates, Database Caplus, Chemical Abstract Service, XP002310235 (1p.).
Jurecka, et al, Synthesis, characterization and extraction behaviours of calyx'4!arene-based phosphonic acids, J. of the Chemical Society, 2002:1370-1377.
Komlev, et al., Phosphorylation of some organic luminophors, Database Caplus, Chemical Abstracts Service, XP002310236 (1p).
Kunsagi-Mate, et al., Complex formation between 1-chloro-4-(trifluoromethyl)benzene (guest) and 4-tert-butylcaliz[4]arenes (host) distally substituted with phosphonic acid or phosphonic ester groups at the lower rim, Tetrahedron, 2002;58(25):5119-5124.
Pugia, et al., Effect of sidearm length upon competitive alkali metal solvent extraction into chloroform by lipophilic crown phosphonic acid monoalkly esters, Analytical Chemistry, 1986;58(13):2723-2726.
Sorori, et al., Lithographic printing plate master for CTP (computer-to-plate) platemaking, Database Caplus, Chemical Abstracts Service, XP002310234 (1 p).
Hong-Wu He et al., "Synthesis Properties and Biological Activity of alpha-(Benzothiazol-2-yl-oxy)", Youji Huaxue (Chinese Journal of Organic Chemistry), 1993, 13:269-272.
Hong-Wu He et al., "A Study to an Organic Phosphorus Compound of Biological Activity Synthesis and biological activity of IV, alpha-[(substituted) benzothiazole-2-oxo] hydrocarbon phosphonate", Yingyong Huaxue (Chinese Journal of Applied Chemistry), 1993, 10(2): 20-23.
M. Gulea et al., "[2,3]-Sigmatropic Rearrangement of Ylides Resulting from the Reaction of a Diazomethylphosphonate with Allyic Sulfides. Synthesis of New alpha-Phosphorylated Unsaturated Sulfides", Synthesis, 1998, 11:1635-1639.

* cited by examiner

Disaggregation with Clioquinol

Disaggregation with 15

Disaggregation with 1

Disaggregation with compound 11

Disaggregation with T = 9:1 ratio of 8 and 10

L929 viability with clioquinol

FIG. 6 Cont'd
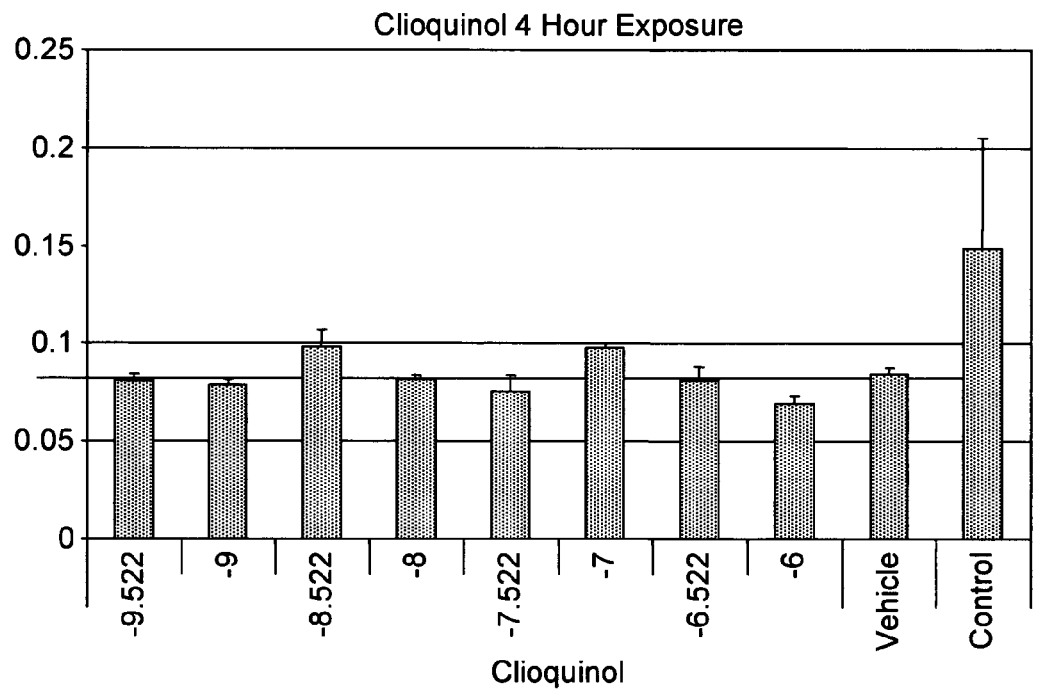
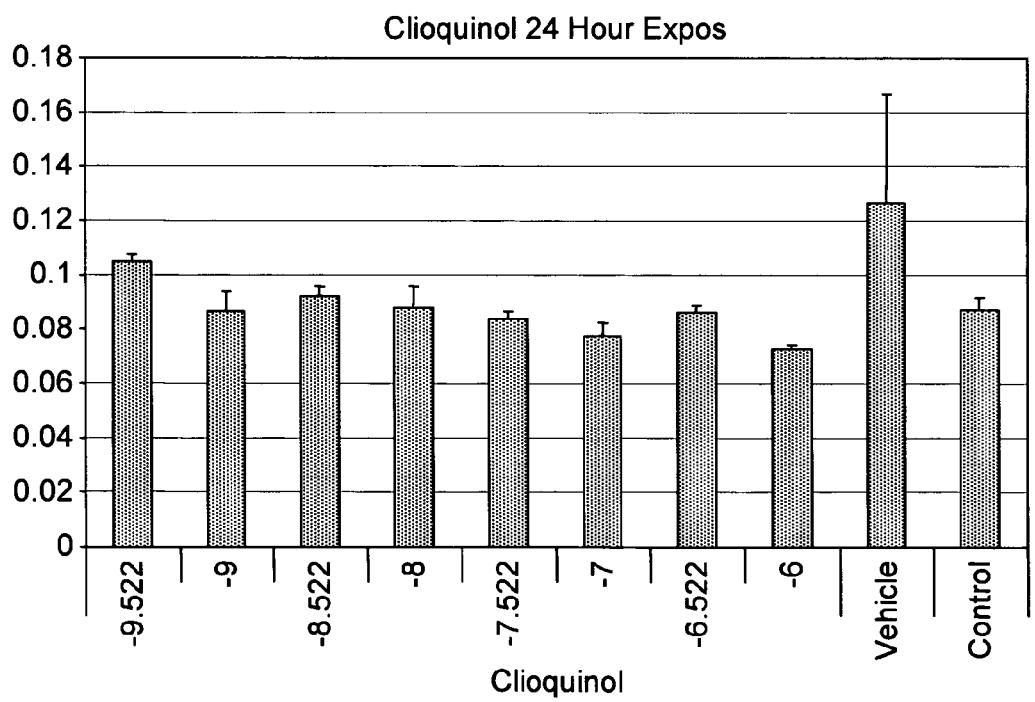

FIG. 7
L929 viability with 15
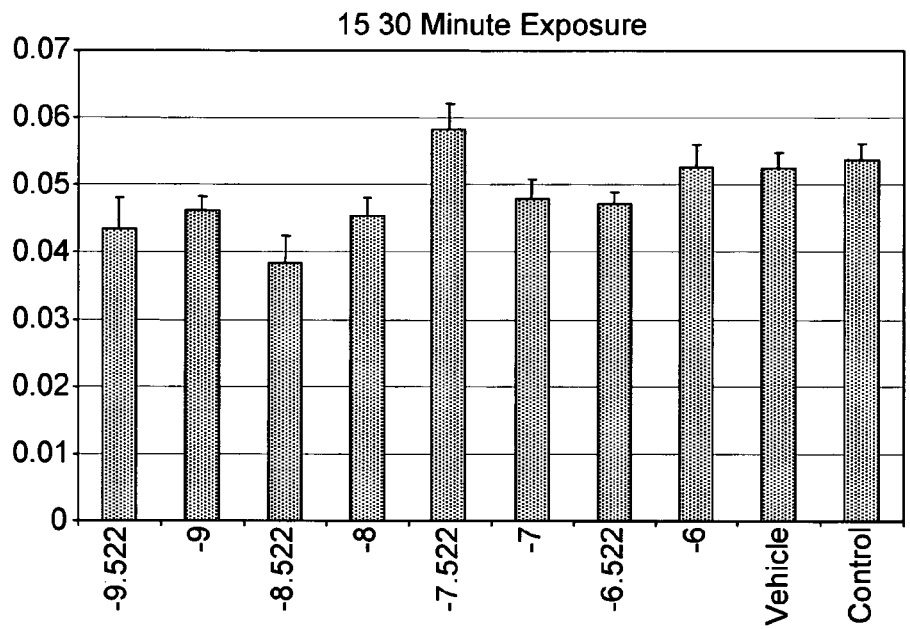
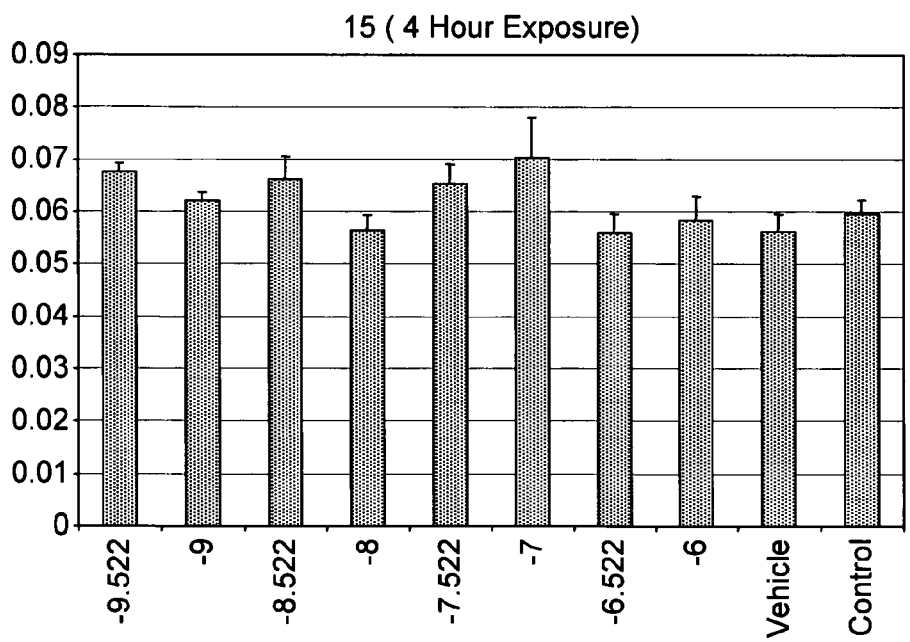

H4 cell viability with 11 using Neutral Red
(Each group starts with control on left hand side)

FIG. 9
H4 cell viability with 1 using Neutral Red
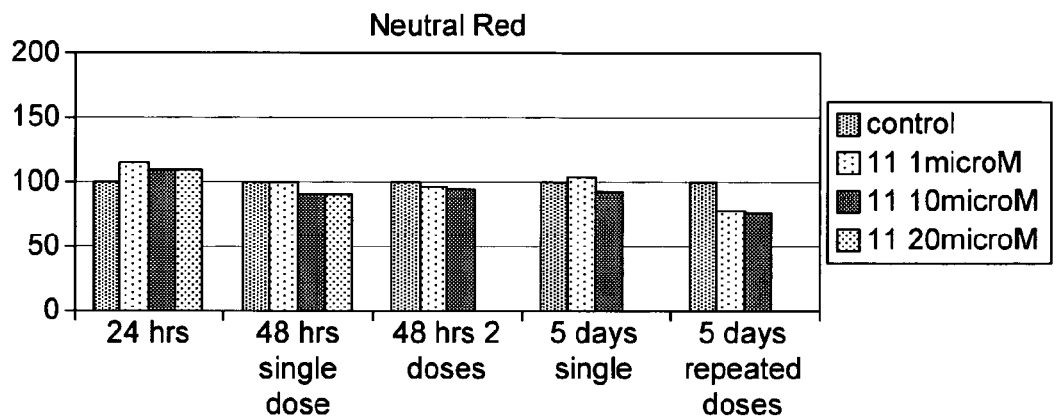
FIG. 10
Cell viability/survival and amyloid accumulation data for 1
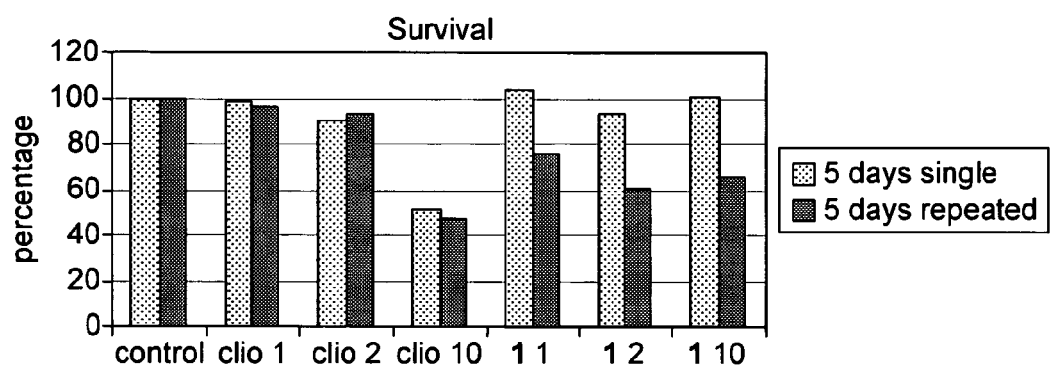
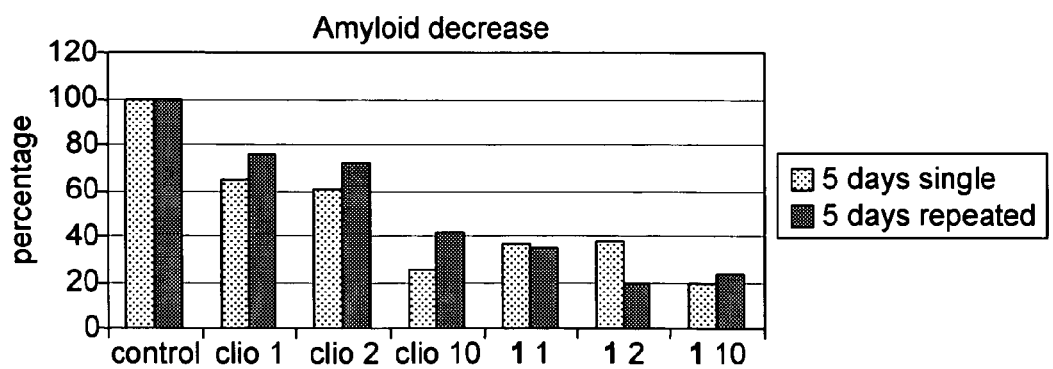

Cell viability/survival and amyloid accumulation data for 11

Cell viability/survival and amyloid accumulation data for T

Cell viability/survival and amyloid accumulation data for 21

Observations on the intracellular distribution of amyloid after incubation with substituted phosphonates

FIG. 15

The figure below shows natural fluorescence of 27 and amyloid labelling in the right and left panels, respectively, after 1μM for 5 days, single dose. Arrows indicate H4 cells with strong amyloid and no 27 signal, arrowheads little amyloid and evidence of 27 in the cytoplasm and nucleus of the H4 cells. There is also overlap in some H4 cells between the 27 and the amyloid lebelling shown by the *

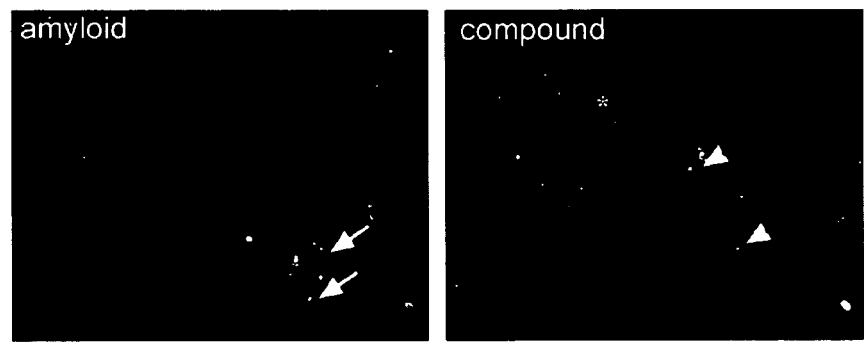

Effects on primary sensory neurons

FIG. 17
Images of primary sendory neurons after exposure to control, 1 and 11
Control 24 hours
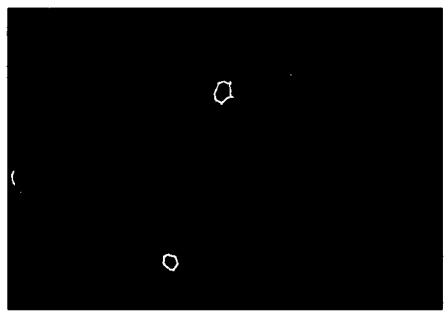
1 24 hours
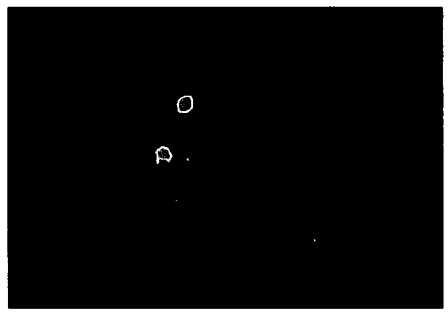
11 24 hours
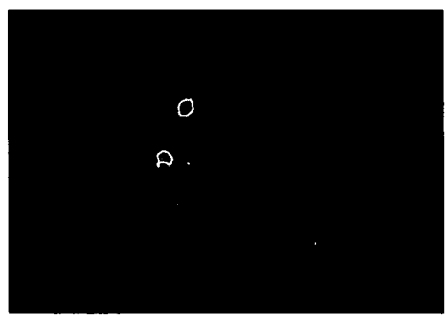

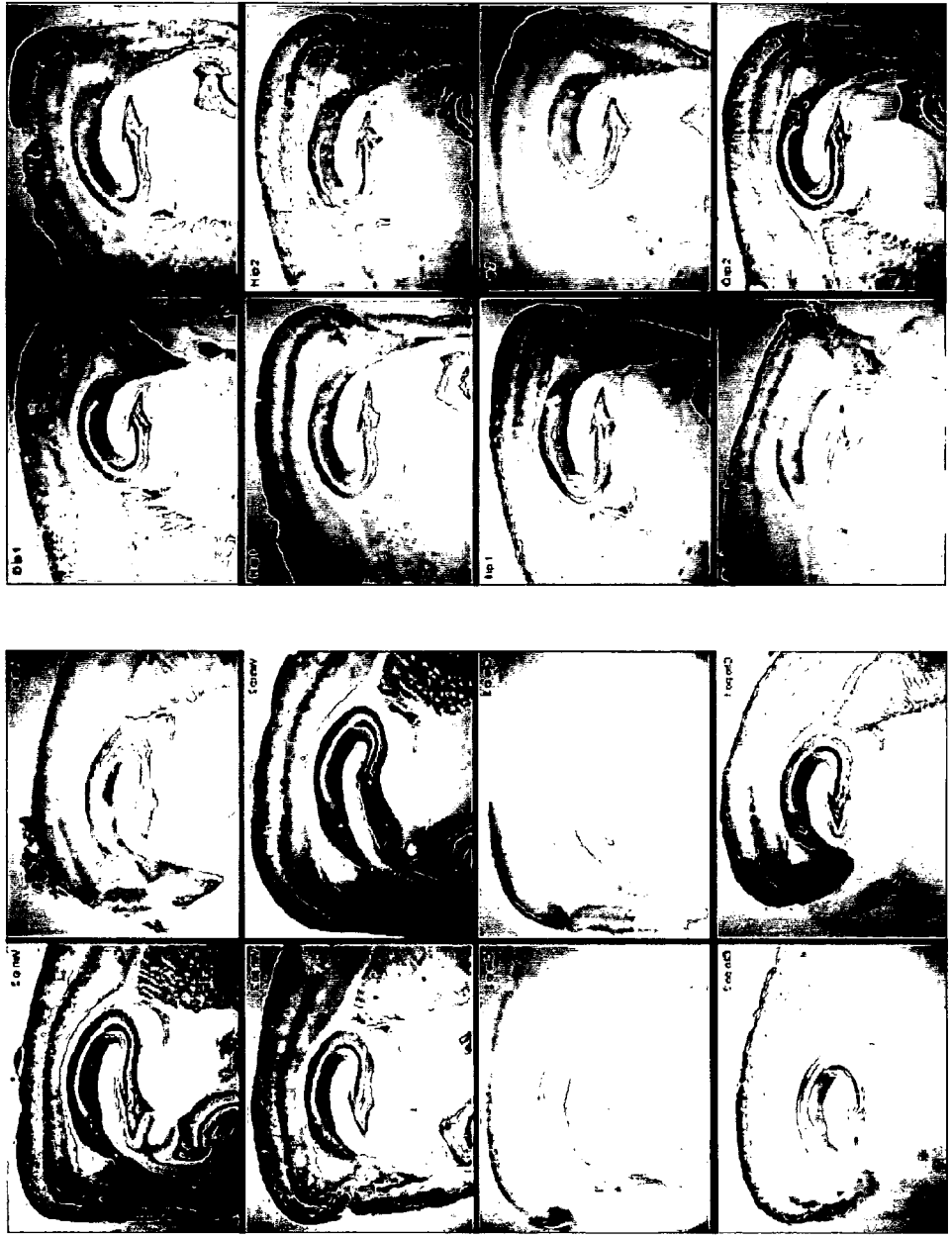
FIG. 18 Autometallographic images of brain parenchyma after exposure to compounds

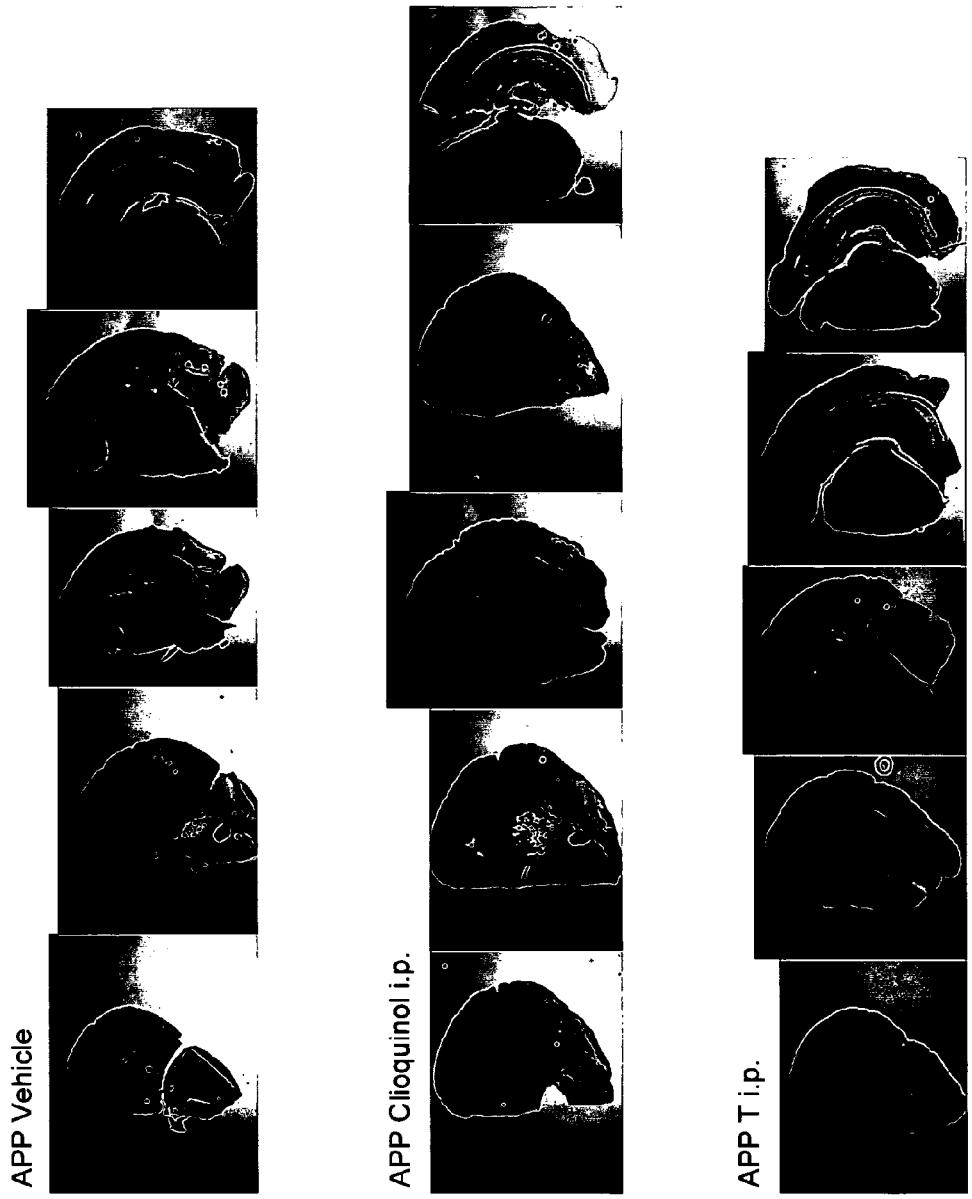

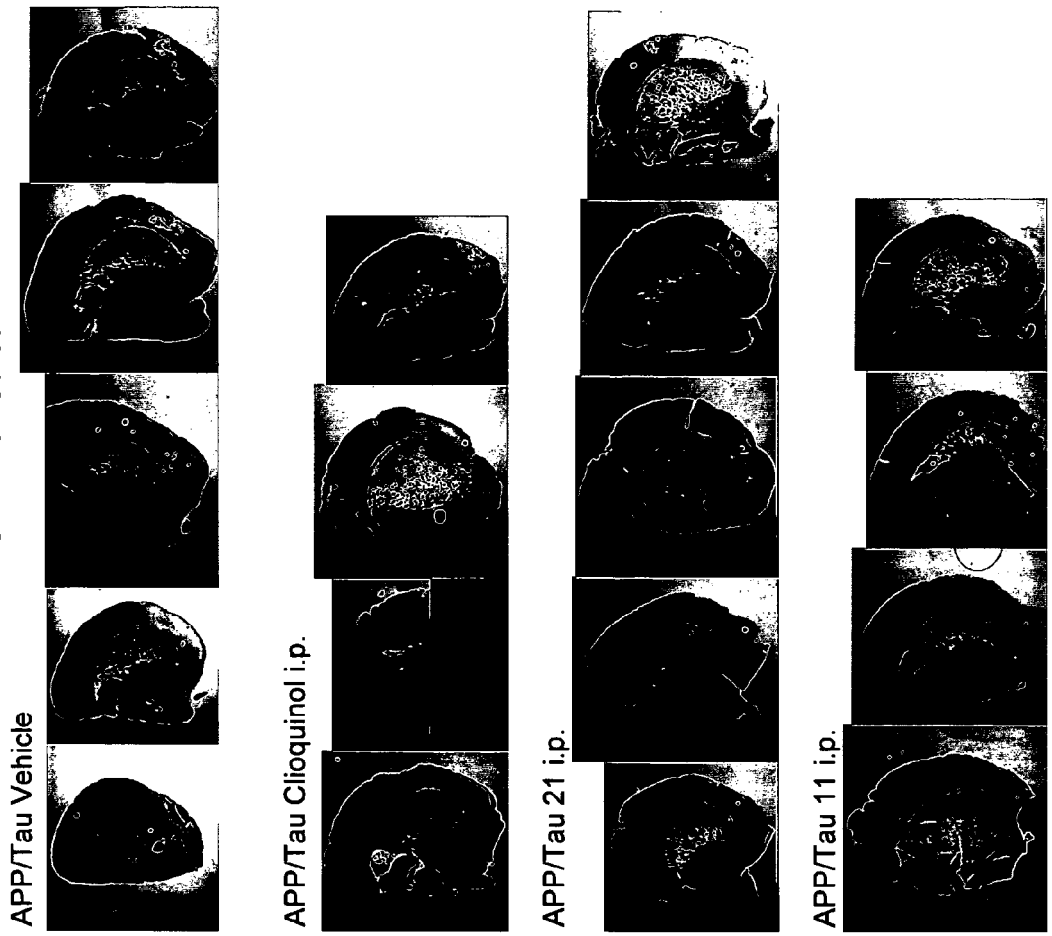

US 8,513,219 B2

SUBSTITUTED PHOSPHONATES AND THEIR USE IN DECREASING AMYLOID AGGREGATES

CROSS-REFERENCE TO RELATED APPLICATIONS

This application is the U.S. National Stage filing of International Application Serial No. PCT/GB2008/001540 filed May 2, 2008, which claims priority to GB Application No. 0708507.9 filed May 2, 2007, each of which is incorporated herein by reference in its entirety.

The invention relates to novel and known substituted phosphonates for use in decreasing amyloid aggregates, particularly for use in the treatment of Alzheimer's disease (AD).

Diseases linked to amyloidosis include, for example, Alzheimer's disease, type 2 diabetes, Huntington's disease and Parkinson's disease. The diseases share a common characteristic whereby abnormal amyloid deposits are found in the affected organs. AD in particular displays abnormal amyloid deposits, typically found as of neuritic plaques in brain parenchyma and amyloidosis in cerebral blood vessels. The A[beta], 42 residue peptide, is the major constituent of these plaques. To date the cause of A[beta] deposits is unknown but a successful treatment of the disease may follow from the prevention of these deposits. Various compounds leading to modulation of the amyloid formation have been reported but so far no compound is available as a treatment. Examples of reports on such compounds deal with aminocarboxylates such as DP-109 J-Y Lee, J E Friedman, I Angel, A Kozak, J-Y Koh, Neurobiology of Aging, 2004, 25, 1315-1321 and WO9916741, desferrioxamine DFO (D R Crapper Maclachlan, A J Dalton, T P A Kruck, M Y Bell, W L Smith W Kalow, D F Andrews Lancet, 1991, 337, 1304). Clioquinol, C C Curtain, K J Barnham and A I Bush, Curr. Med. Chem.-Immun., Endoc. & Metab. Agents, 2003, 3, 309-315, US2006074104; N-thiazolyl amides, FR2865206; phosphonocarboxylate US2006135479; amine compounds: US2004077867, benzothiepine derivatives US2002128308; succinate esters US2006281692, benzoate an benzamide compounds US2006167108; bi- and tricyclic pyridine derivatives WO9825930; pyrazolylpyrimidines WO03080609.

One possible drug Clioquinol, has been shown to reverse the formation of plaques. Clioquinol chelates zinc and copper in vitro. Copper and zinc have particularly high concentration in the β-amyloid plaques in the brains of AD patients.

Clioquinol was approved by the FDA as an anti-biotic and anti-fungal agent, but was removed from the market over 30 years ago due to adverse side effects including the loss of vitamin B-12. A clinical trial using clioquinol together with vitamin B-12 was conducted to determine whether this drug is useful in the treatment of Alzheimer's without the previously seen side effects. Other side effects included eye damage with long term usage and nerve damage and loss of sensitivity. The first clinical trials of clioquinol (known as PTB1 in these trials) reached the final stages, when it was discovered that the PTB1 manufacturing process contained mutagenic impurities that could not be removed to acceptable levels. Thus, PTB1 trials were ceased. A follow on compound, known as PTB2 was developed, and has now finished phase 1 trials, although the results of this are unknown.

Thus, there remains a need for a way of reducing amyloid plaques in diseases, such as AD, without the adverse side effects seen in trials of the drugs mentioned above. In addition, there is still a clear need for improved therapies that not only improve on current treatment with regard to cognitive defects but also reduce side effects.

Accordingly, the present invention provides novel and known compounds of general formula I, described as fluorescent phosphonates in PCT publication number WO2004/101579, and the preparation and use of these novel and known compounds of general formula I for medical treatments of diseases linked to amyloidosis and compositions comprising such compounds.

The current invention is based on evidence generated showing that substituted phosphonates promote disaggregation of amyloidic aggregates, amyloidic load in cellular systems expressing amyloid, and amyloid plaques and reduce parenchymal zinc in the brain and therefore these compounds may provide treatments for disease states linked to amyloidosis and linked to zinc.

In a first aspect of the present invention, there is provided a compound of general formula I for use in medicine. Such compounds have been shown to be useful in the disaggregation of amyloidic deposits.

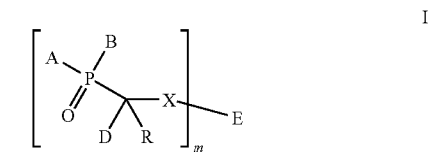

I

Examples of specific compounds for use in the invention are tabulated below in Table 1. Novel compounds 4, 5a, 6, 7a, 8, 8a, 14 and 10 are also provided.

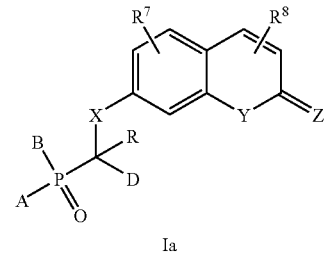

Ia

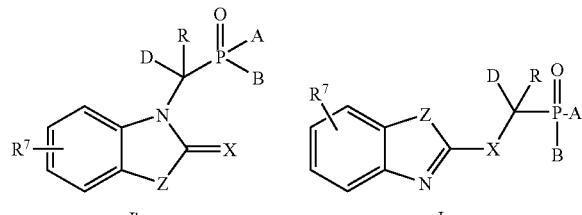

Ib            Ic

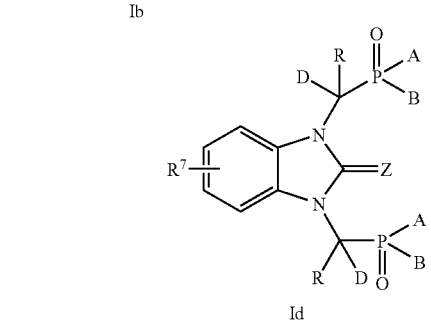

Id

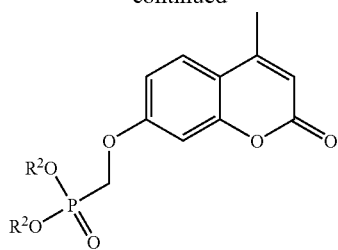

Compound 1 R²/R² = Et/Et
Compound 2 R²/R² = Et/H
Compound 3 R²/R² = H/H

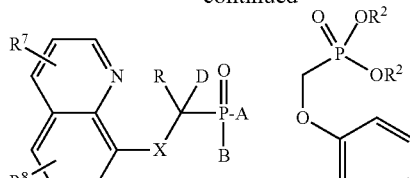

Ih

Compound 11
R² = Et/H

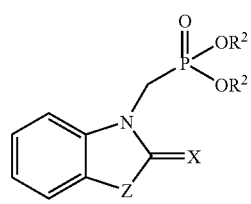
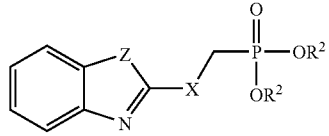

Compound 4 X = O, Z = O
Compound 5 X = S, Z = O
Compound 6 X = O, Z = S
Compound 7 X = S, Z = S
Compound 8 X = O, Z = NH
Compound 9 X = S, Z = NH
R² = Et Compound 4a X = O, Z = O
Compound 5a X = S, Z = O
Compound 6a X = O, Z = S
Compound 7a X = S, Z = S
Compound 8a X = O, Z = NH
Compound 9a X = S, Z = NH
R² = Et

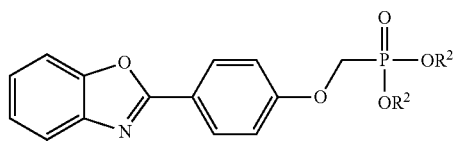

Compound 12
R² = Et/H

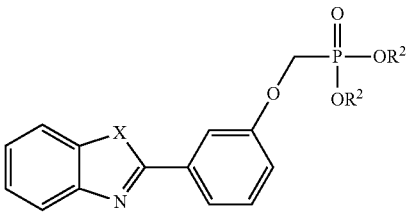

Compound 13 X = O
Compound 14 X = S
R² = Et/H

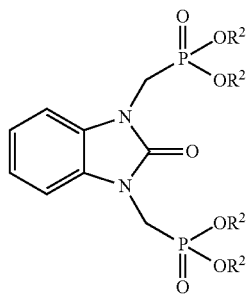
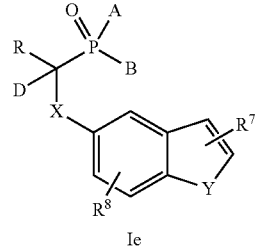

Compound 10
R² = Et

Ie

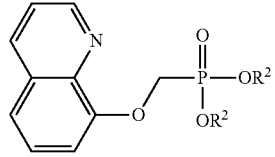

Compound 15 R²/R² = Et
Compound 16 R²/R² = Na

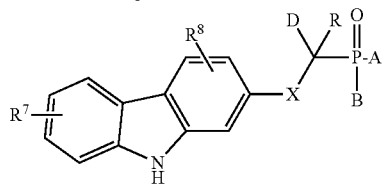

Ii

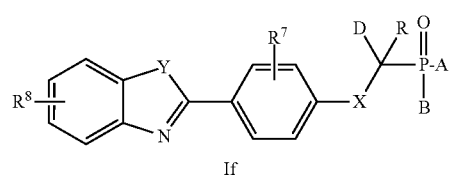

If

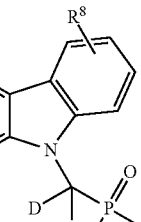

Ij

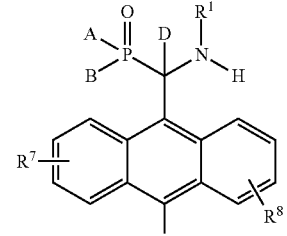

Ik

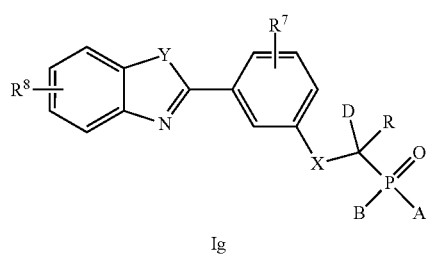

Ig

-continued

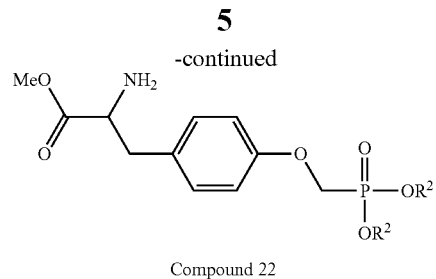
Compound 22

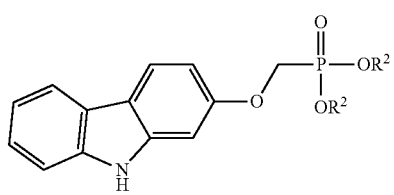
Compound 17 $R^2/R^2$ = Et
Compound 18 $R^2/R^2$ = H

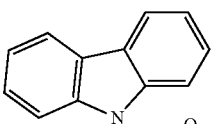
Compound 19 $R^2/R^2$ = Et
Compound 20 $R^2/R^2$ = H

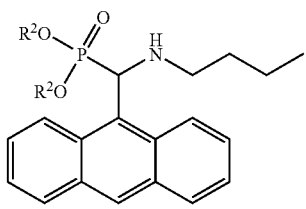
Compound 21 $R^2/R^2$ = Et

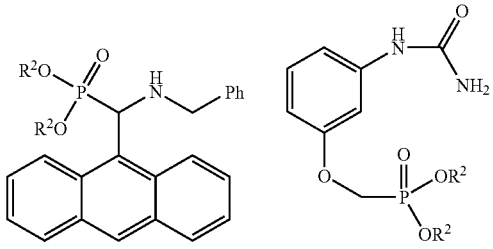
Compound 23  Compound 24

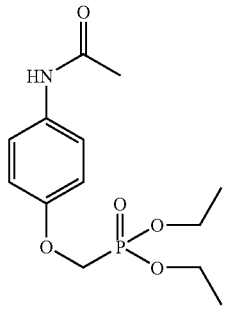
Compound 25

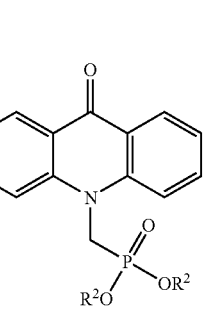
Compound 26

-continued

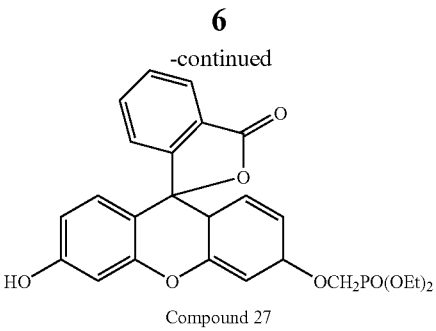
Compound 27

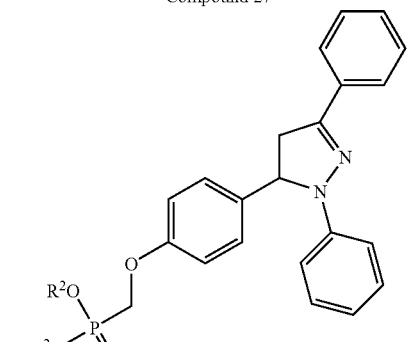
Compound 28 wherein R is hydrogen or a substituted or unsubstituted linear or branched $C_{1-40}$ alkyl, aryl or heteroaryl, preferably $C_{1-20}$ alkyl, more preferably $C_{1-12}$ alkyl, most preferably $C_{1-6}$, i.e. $C_1$, $C_2$, $C_3$, $C_4$, $C_5$ or $C_6$ alkyl; E is a substituted or unsubstituted linear or branched $C_{1-40}$ alkyl, aryl, heteroaryl, or hydrogen where X is O, S, or $NR^1$ or when E is aryl or heteroaryl, X can be N integral to the aryl or heteroaryl ring; wherein $R^1$ is a hydrogen, a linear or branched $C_{1-40}$ alkyl, preferably $C_{1-20}$ alkyl, more preferably $C_{1-12}$ alkyl, most preferably $C_{1-6}$, i.e. $C_1$, $C_2$, $C_3$, $C_4$, $C_5$ or $C_6$ alkyl, $C_{2-40}$ alkenyl, preferably $C_{2-20}$ alkenyl, more preferably $C_{2-12}$ alkenyl, most preferably $C_{2-6}$ i.e. $C_2$, $C_3$, $C_4$, $C_5$ or $C_6$ alkenyl or $C_{2-40}$ alkynyl, preferably $C_{2-20}$ alkynyl, more preferably $C_{2-12}$ alkynyl, most preferably $C_{2-6}$ i.e. $C_2$, $C_3$, $C_4$, $C_5$ or $C_6$ alkynyl group, an aryl, a heteroaryl or $C_{1-40}$ alkylaryl, preferably $C_{1-20}$ alkylaryl, more preferably $C_{1-12}$ alkylaryl, most preferably $C_{1-6}$, i.e. $C_1$, $C_2$, $C_3$, $C_4$, $C_5$ or $C_6$ alkylaryl or alkylheteroaryl, preferably $C_{1-20}$ alkylaryl or alkylheteroaryl, more preferably $C_{1-12}$ alkylaryl or alkylheteroaryl, most preferably $C_{1-6}$, i.e. $C_1$, $C_2$, $C_3$, $C_4$, $C_5$ or $C_6$ alkylaryl or alkylheteroaryl group and where A and B are independently $OR^2$, $SR^2$, $NR^3R^4$ where $R^2$, $R^3$, and $R^4$ are each independently hydrogen, a linear or branched $C_{1-40}$ alkyl, preferably $C_{1-20}$ alkyl, more preferably $C_{1-12}$ alkyl, most preferably $C_{1-6}$, i.e. $C_1$, $C_2$, $C_3$, $C_4$, $C_5$ or $C_6$ alkyl, $C_{2-40}$ alkenyl, preferably $C_{2-20}$ alkenyl, more preferably $C_{2-12}$ alkenyl, most preferably $C_{2-6}$ i.e. $C_2$, $C_3$, $C_4$, $C_5$ or $C_6$ alkenyl or $C_{2-40}$ alkynyl, preferably $C_{2-20}$ alkynyl, more preferably $C_{2-12}$ alkynyl, most preferably $C_{2-6}$ i.e. $C_2$, $C_3$, $C_4$, $C_5$ or $C_6$ alkynyl group, an aryl or $C_{1-40}$ alkylaryl, preferably $C_{1-20}$ alkylaryl, more preferably $C_{1-12}$ alkylaryl, most preferably $C_{1-6}$, i.e. $C_1$, $C_2$, $C_3$, $C_4$, $C_5$ or $C_6$ alkylaryl group, or optionally a complex metal ion $M^{n+}/n$ wherein n is an integer from 1 to 8, or a linear or branched $C_{1-40}$ $NR^5R^6$ terminated alkyl chain, preferably $C_{1-20}NR^5R^6$ terminated alkyl chain, more preferably $C_{1-12}NR^5R^6$ terminated alkyl chain, most preferably $C_{1-6}$, i.e. $C_1$, $C_2$, $C_3$, $C_4$, $C_5$ or $C_6NR^5R^6$ terminated alkyl chain where $R^5$ and $R^6$ are each independently hydrogen, a linear or branched $C_{1-40}$ alkyl, preferably $C_{1-20}$ alkyl, more preferably $C_{1-12}$ alkyl, most preferably $C_{1-6}$, i.e. $C_1$, $C_2$, $C_3$, $C_4$, $C_5$ or $C_6$ alkyl; and wherein m is an integer from 1 to 8; and wherein D is hydrogen or a linear or branched $C_{1-40}$ alkyl, preferably $C_{1-20}$ alkyl, more preferably $C_{1-12}$ alkyl, most preferably $C_{1-6}$, i.e. $C_1$, $C_2$, $C_3$, $C_4$, $C_5$ or $C_6$ alkyl, $C_{2-40}$ alkenyl, preferably $C_{2-20}$ alkenyl, more preferably $C_{2-12}$ alkenyl, most preferably $C_{2-6}$ i.e. $C_2$, $C_3$, $C_4$, $C_5$ or $C_6$ alkenyl or $C_{2-40}$ alkynyl, preferably $C_{2-20}$ alkynyl, more preferably $C_{2-12}$ alkynyl, most preferably $C_{2-6}$ i.e. $C_2$, $C_3$, $C_4$, $C_5$ or $C_6$ alkynyl group, an aryl, a heteroaryl or $C_{1-40}$ alkylaryl or alkylheteroaryl, preferably $C_{1-20}$ alkylaryl or alkylheteroaryl, more preferably $C_{1-12}$ alkylaryl or alkylheteroaryl, most preferably $C_{1-6}$, i.e. $C_1$, $C_2$, $C_3$, $C_4$, $C_5$ or $C_6$ alkylaryl or alkylheteroaryl group or a linear or branched $C_{1-40}$ alkyl $NR^5R^6$ chain, preferably $C_{1-20}$ alkyl $NR^5R^6$ chain, more preferably $C_{1-12}$ alkyl $NR^5R^6$ chain, most preferably $C_{1-6}$, i.e. $C_1$, $C_2$, $C_3$, $C_4$, $C_5$ or $C_6$ alkyl $NR^5R^6$ chain, or a linear or branched $C_{1-40}$ mono or di alkyl ester, preferably $C_{1-20}$ mono or di alkyl ester, more preferably $C_{1-12}$ mono or di alkyl ester, most preferably $C_{1-6}$, i.e. $C_1$, $C_2$, $C_3$, $C_4$, $C_5$ or $C_6$ mono or di alkyl ester $C_{1-40}$ alkylphosphonate, preferably $C_{1-20}$ alkylphosphonate, more preferably $C_{1-12}$ alkylphosphonate, most preferably $C_{1-6}$, i.e. $C_1$, $C_2$, $C_3$, $C_4$, $C_5$ or $C_6$ alkylphosphonate or a linear or branched $C_{1-40}$ alkylphosphonic acid, preferably $C_{1-20}$ alkylphosphonic acid, more preferably $C_{1-12}$ alkylphosphonic acid, most preferably $C_{1-6}$, i.e. $C_1$, $C_2$, $C_3$, $C_4$, $C_5$ or $C_6$ alkylphosphonic acid Y and Z are O, S, or $NR^1$. $R^7$ and $R^8$ represent one or more ring substituents which can be a hydrogen, a halide, a linear or branched $C_{1-40}$ alkyl, preferably $C_{1-20}$ alkyl, more preferably $C_{1-12}$ alkyl, most preferably $C_{1-6}$, i.e. $C_1$, $C_2$, $C_3$, $C_4$, $C_5$ or $C_6$ alkyl, $C_{2-40}$ alkenyl, preferably $C_{2-20}$ alkenyl, more preferably $C_{2-12}$ alkenyl, most preferably $C_{2-6}$ i.e. $C_2$, $C_3$, $C_4$, $C_5$ or $C_6$ alkenyl or $C_{2-40}$ alkynyl, preferably $C_{2-20}$ alkynyl, more preferably $C_{2-12}$ alkynyl, most preferably $C_{2-6}$ i.e. $C_2$, $C_3$, $C_4$, $C_5$ or $C_6$ alkynyl group, an aryl, a heteroaryl or $C_{1-40}$ alkylaryl or alkylheteroaryl, preferably $C_{1-20}$ alkylaryl or alkylheteroaryl, more preferably $C_{1-12}$ alkylaryl or alkylheteroaryl, most preferably $C_{1-6}$, i.e. $C_1$, $C_2$, $C_3$, $C_4$, $C_5$ or $C_6$ alkylaryl or alkylheteroaryl group, a nitrile, a sulfonic acid or salt of sulfonic acid, a carboxy, an oxo, a carboxyalkyl, a carboxyalkoxy, a carboxylalkylamino, carboxyalkylthio, an amide, a sulfonamide, a $C_{1-6}$ alkylalkoxy, a $C_{1-6}$alkylamino group, $OR^2$, $SR^2$, $NR^3R^4$ where $R^2$, $R^3$, and $R^4$ are each independently hydrogen, a linear or branched $C_{1-40}$ alkyl, preferably $C_{1-20}$ alkyl, more preferably $C_{1-12}$ alkyl, most preferably $C_{1-6}$, i.e. $C_1$, $C_2$, $C_3$, $C_4$, $C_5$ or $C_6$ alkyl, $C_{2-40}$ alkenyl, preferably $C_{2-20}$ alkenyl, more preferably $C_{2-12}$ alkenyl, most preferably $C_{2-6}$ i.e. $C_2$, $C_3$, $C_4$, $C_5$ or $C_6$ alkenyl or $C_{2-40}$ alkynyl, preferably $C_{2-20}$ alkynyl, more preferably $C_{2-12}$ alkynyl, most preferably $C_{2-6}$ i.e. $C_2$, $C_3$, $C_4$, $C_5$ or $C_6$ alkynyl group, an aryl or $C_{1-40}$ alkylaryl, preferably $C_{1-20}$ alkylaryl, more preferably $C_{1-12}$ alkylaryl, most preferably $C_{1-6}$, i.e. $C_1$, $C_2$, $C_3$, $C_4$, $C_5$ or $C_6$ alkylaryl group.

In an alternative embodiment, formula I can be represented as:

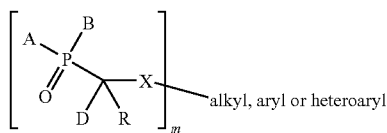

wherein R is hydrogen or a linear or branched substituted or unsubstituted $C_{1-40}$ alkyl; X is O, S or N, which can be integral to the aryl or heteroaryl ring or $NR^1$ where $R^1$ is a hydrogen, a linear or branched $C_{1-40}$ alkyl, $C_{2-40}$ alkenyl, or $C_{2-40}$ alkynyl, or aryl, a heteroaryl or $C_{1-40}$ alkylaryl or alkylheteroaryl; one or both of A and B is $OR^2$, $SR^2$, $NR^3$, $R^4$ where $R^2$, $R^3$ and $R^4$ are each independently hydrogen, a linear or branched $C_{1-40}$ alkyl, $C_{2-40}$ alkenyl, $C_{2-40}$ alkynyl, $C_{1-40}$ alkylaryl or optionally a complex metal ion $M^{n+}/n$ wherein n is an integer from 1 to 8, or a linear or branched $C_{1-40}$ $NR^5R^6$ terminated alkyl chain, where $R^5$ and $R^6$ are each independently hydrogen, a linear or branched $C_{1-40}$ alkyl; m is an integer from 1 to 8; and wherein D is hydrogen or a linear or branched $C_{1-40}$ alkyl, $C_{2-40}$ alkenyl, $C_{2-40}$ alkynyl, an aryl, a heteroaryl or $C_{1-40}$ alkylaryl or alkylheteroaryl or a linear or branched $C_{1-40}$ alkyl $NR^5R^6$ chain or a linear or branched $C_{1-40}$ mono or di alkyl ester or di alkyl ester $C_{1-40}$ alkylphosphonate or a linear or branched $C_{1-40}$ alkylphosphonic acid.

In the context of the present invention, $C_{1-40}$ alkyl, preferably $C_{1-20}$ alkyl, more preferably $C_{1-12}$ alkyl, most preferably $C_{1-6}$, i.e. $C_1$, $C_2$, $C_3$, $C_4$, $C_5$, or $C_6$ alkyl refers to a straight, branched or cyclic hydrocarbon chain having from one to forty carbon atoms. The $C_{1-40}$ alkyl, preferably $C_{1-20}$ alkyl, more preferably $C_{1-12}$ alkyl, most preferably $C_{1-6}$, i.e. $C_1$, $C_2$, $C_3$, $C_4$, $C_5$, or $C_6$ alkyl, group may be substituted with one or more substituents selected from nitro, chloro, fluoro, bromo, nitrile, sulfonic acid or salt of sulfonic acid, carboxy, oxo, aryl, heteroaryl, carboxyalkyl, carboxyalkoxy, carboxylalkylamino, carboxyalkylthio, $C_{1-6}$ alkoxy, di $C_{1-40}$ alkyl phosphonate, $C_{1-40}$ alkyl phosphonate, phosphonic acid, amino, amino $C_{1-40}$ alkyl or amino di($C_{1-40}$ alkyl). Examples include methyl, ethyl, isopropyl, n-propyl, butyl, tert-butyl, n-hexyl, n-decyl, n-dodecyl, cyclohexyl, octyl, iso-octyl, hexadecyl, octadecyl, iso-octadecyl and docosyl. A $C_{1-12}$-alkyl group has from one to twelve carbon atoms.

In the context of the present invention, $C_{2-40}$ alkenyl, preferably $C_{2-20}$ alkenyl, more preferably $C_{2-12}$ alkenyl, most preferably $C_{2-6}$ i.e. $C_2$, $C_3$, $C_4$, $C_5$ or $C_6$ alkenyl refers to a straight, branched or cyclic hydrocarbon chain having from one to forty carbon atoms and including at least one carbon-carbon double bond. The $C_{2-40}$ alkenyl, preferably $C_{2-20}$ alkenyl, more preferably $C_{2-12}$ alkenyl, most preferably $C_{2-6}$ i.e. $C_2$, $C_3$, $C_4$, $C_5$ or $C_6$ alkenyl, group may be substituted with one or more substituents selected from nitro, chloro, fluoro, bromo, nitrile, sulfonic acid or salt of sulfonic acid, carboxy, oxo, alkyl, carboxyalkyl, carboxyalkoxy, carboxylalkylamino, carboxyalkylthio, $C_{1-6}$-alkoxy, di $C_{1-40}$ alkyl phosphonate, $C_{1-40}$ alkyl phosphonate, phosphonic acid, amino, amino $C_{1-40}$-alkyl or amino di($C_{1-40}$-alkyl). Examples include ethenyl, 2-propenyl, cyclohexenyl, octenyl, iso-octenyl, hexadecenyl, octadecenyl, iso-octadecenyl and docosenyl.

In the context of the present invention, $C_{2-40}$ alkynyl, preferably $C_{2-20}$ alkynyl, more preferably $C_{2-12}$ alkynyl, most preferably $C_{2-6}$ i.e. $C_2$, $C_3$, $C_4$, $C_5$ or $C_6$ alkynyl refers to a straight, branched or cyclic hydrocarbon chain having from one to forty carbon atoms and including at least one carbon-carbon triple bond. The $C_{2-40}$ alkynyl, preferably $C_{2-20}$ alkynyl, more preferably $C_{2-12}$ alkynyl, most preferably $C_{2-6}$ i.e. $C_2$, $C_3$, $C_4$, $C_5$ or $C_6$ alkynyl, group may be substituted with one or more substituents selected from nitro, chloro, fluoro, bromo, nitrile, sulfonic acid or salt of sulfonic acid, carboxy, oxo, carboxyalkyl, carboxyalkoxy, carboxyalkylamino, carboxyalkylthio, $C_{1-6}$-alkoxy, di $C_{1-40}$ alkyl phosphonate, $C_{1-40}$ alkyl phosphonate, phosphonic acid, amino, amino $C_{1-40}$-alkyl or amino di($C_{1-40}$-alkyl). Examples include ethynyl, 2-propynyl octynyl, iso-octynyl, hexadecynyl, octadecynyl, iso-octadecynyl and docosynyl.

$C_{1-6}$ alkoxy refers to a straight or branched hydrocarbon chain having from one to six carbon atoms and attached to an oxygen atom. Examples include methoxy, ethoxy, propoxy, tert-butoxy and n-butoxy.

The term aryl refers to a five or six membered cyclic, 8-10 membered bicyclic or 10-14 membered tricyclic group or up to a 10 fused ringed polyaromatic system with aromatic character and includes systems which contain one or more heteroatoms, for example, N, O or S. The aryl group may be substituted with one or more substituents selected from nitro, chloro, fluoro, bromo, nitrile, sulfonic acid or salt of sulfonic acid, carboxy, oxo, alkyl, alkoxy, carboxyalkyl, carboxyalkoxy, carboxylalkylamino, carboxyalkylthio, $C_{1-6}$-alkoxy, di $C_{1-40}$ alkyl phosphonate, $C_{1-40}$ alkyl phosphonate, phosphonic acid, amino, amino $C_{1-40}$-alkyl or amino di($C_{1-40}$-alkyl).

Heteroaryl, as used herein, is an aromatic group that contains at least one heteroatom (a non-carbon atom forming the ring structure) and is optionally a single, two, three, four, five, six ringed structure or a fused 2-, 3-, 4-, 5-, 6-, 7- or 8-ring structure. Examples include pyrrolyl, pyridyl, thienyl, furanyl, oxazolyl, isoazolyl, oxadiazolyl, imidazolyl, benzoxazolyl, benzothiazolyl, benzimidazolyl, quinolyl, benzofuranyl, indolyl, carbazolyl, coumarins and benzocoumarins. The heteroaryl group may be substituted with one or more substituents selected from nitro, chloro, fluoro, bromo, nitrile, sulfonic acid or salt of sulfonic acid, carboxy, oxo, alkyl, alkoxy, carboxyalkyl, carboxyalkoxy, carboxylalkylamino, carboxyalkylthio, $C_{1-6}$-alkoxy, di $C_{1-40}$ alkyl phosphonate, $C_{1-40}$ alkyl phosphonate, phosphonic acid, amino, amino $C_{1-40}$-alkyl or amino di($C_{1-40}$-alkyl). Such substituents are typically used to modify the spectral properties, affinity, selectivity, solubility or any combination of these factors.

The term $C_{1-40}$ alkylaryl, preferably $C_{1-20}$ alkylaryl, more preferably $C_{1-12}$ alkylaryl, most preferably $C_{1-6}$, i.e. $C_1$, $C_2$, $C_3$, $C_4$, $C_5$ or $C_6$ alkylaryl, group refers to a straight or branched hydrocarbon chain having from one to forty carbon atoms linked to an aryl group. The $C_{1-40}$ alkylaryl, preferably $C_{1-20}$ alkylaryl, more preferably $C_{1-12}$ alkylaryl, most preferably $C_{1-6}$, i.e. $C_1$, $C_2$, $C_3$, $C_4$, $C_5$ or $C_6$ alkylaryl, group may be substituted with one or more substituents selected from nitro, chloro, fluoro, bromo, nitrile, sulfonic acid or salt of sulfonic acid, carboxy, oxo, carboxyalkyl, carboxyalkoxy, carboxylalkylamino, carboxyalkylthio, $C_{1-6}$-alkoxy, di $C_{1-40}$ alkyl phosphonate, $C_{1-40}$ alkyl phosphonate, phosphonic acid, amino, amino $C_{1-40}$-alkyl or amino di($C_{1-40}$-alkyl). Examples include benzyl, phenylethyl and pyridylmethyl. In a $C_{1-8}$ alkylaryl group, the alkyl chain has from one to eight carbon atoms.

Compounds in which R and D are each independently hydrogen, X is either oxygen or a nitrogen with hydrogen attached or sulfur, and A and B are $OR^9$ where $R^9$ is a hydrogen, a $C_{1-6}$ alkyl or an optionally complex metal ion $M^{n+}/n$ wherein n is an integer from 1 to 8; and compounds in which R is hydrogen, X is either oxygen or nitrogen, A is a alkylaryl group, B is a known aryl or heteroaryl fluorophore and A and B are $OR^2$ where $R^2$ is hydrogen, a $C_{1-6}$ alkyl or an optionally complex metal ion $M^{n+}/n$ wherein n is an integer from 1 to 8; are especially preferred.

In a preferred embodiment of the first aspect, the compound is one or more selected from the group consisting of formula Ia, Ib, Ic, Id, Ie, Ih or Ik. More preferably, the compound is one or more selected from the group consisting of compound 1, 8, 8a, 10, 11, 15, 21, 23, 26 and 27.

The compound of the first aspect may be used in decreasing amyloid aggregates in vitro or in vivo. By this it is meant that aggregates of the amyloid peptide may be dispersed, or disaggregated, by the compound of the invention. Thus, the size, number and/or density of aggregates will be reduced.

A further embodiment of the first aspect provides the compounds of the invention for use in the treatment of a disease characterised by amyloid deposition. Such a disease may be Alzheimer's disease, type 2 diabetes, Huntington's disease, Parkinson's disease and others. Most particularly, the compounds of the invention may be used for treating Alzheimer's disease.

By amyloid deposition, it is meant a build up of aggregates of amyloid, also known as amyloid plaques. The compounds of the invention may treat such diseases by reducing the size, density and/or number of plaques in a subject with the disease.

A second aspect of the invention provides the use of a compound of general formula I in the manufacture of a medicament for use in the treatment of a disease characterised by amyloid deposition. Such a disease, preferably, is Alzheimer's disease.

In a preferred embodiment of the second aspect, the compound is selected from the group consisting of formula Ia, Ib, Ic, Id, Ie, and Ik. More preferably the compound is one or more selected from the group consisting of compounds 1 to 28 and 4a to 9a. Most preferably the compound is one or more selected from the group consisting of compounds 1, 8, 8a, 10, 11, 15, 21, 23, 26 and 27.

As a third aspect, the invention provides novel compounds of formula I. Specifically, such compounds are compounds 4, 5a, 6, 7a, 8, 8a, 14 and 10, as defined in table 1.

The present invention provides these novel compounds for use in medicine and in the manufacture of a medicament for use in the treatment of a disease characterised by amyloid deposition. Such a disease may be Alzheimer's disease. The compounds may be used in decreasing amyloid aggregates, in vitro or in vivo.

The invention also provides a composition comprising a compound of general formula I and the composition in the manufacture of a medicament for use in the treatment of a disease characterised by amyloid deposition.

Medicaments in accordance with the invention will usually be supplied as part of a sterile, pharmaceutical composition which will normally include a pharmaceutically acceptable carrier. This pharmaceutical composition may be in any suitable form, (depending upon the desired method of administering it to a subject).

It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example by the oral (including buccal or sublingual), topical (including buccal, sublingual or transdermal), or parenteral (including subcutaneous, intramuscular, intravenous or intradermal) route. Such compositions may be prepared by any method known in the art of pharmacy, for example by admixing the active ingredient with the carriers) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions)

Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc.

For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3(6):318 (1986).

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administration to the eye include eye drops wherein the active ingredient is dissolved or suspended in a suitable carrier, especially an aqueous solvent.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Dosages of the substances of the present invention can vary between wide limits, depending upon the disease or disorder to be treated, the condition of the individual to be treated, etc. and a veterinarian will ultimately determine appropriate dosages to be used. The dosage may be repeated as often as appropriate. If side effects develop the amount and/or frequency of the dosage can be reduced, in accordance with normal clinical practice.

All preferred features of each aspect apply to all other aspects mutatis mutandis.

The invention will now be described by way of the following non-limiting examples, with reference to the Figures, in which:

FIG. 9 Shows human neuroblastoma cell line H4 cell viability with compound 1 using Neutral Red;

FIG. 10 Shows human neuroblastoma cell line cell viability/survival and amyloid accumulation data for compound 1;

FIG. 15 Shows natural fluorescence of compound 27 and amyloid labelling, in the absence of compound 27;

FIG. 17 Shows images of primary sensory neurons after exposure to control, compound 1 and compound 11;

FIG. 18 Shows autometallographic images of brain parenchyma after exposure to compounds 11, T, 21, 1 and clioquinol;

Figure 1:
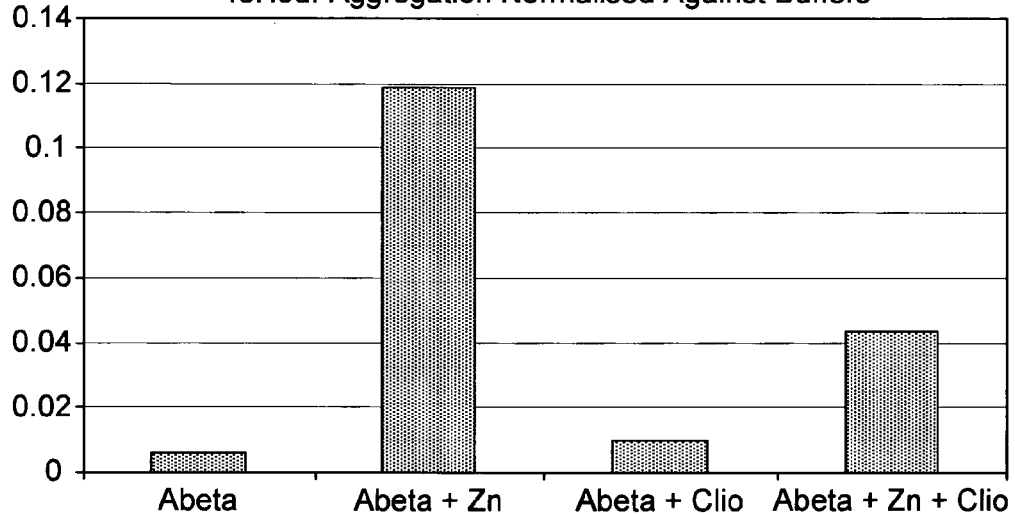
FIG. 1 Shows the disaggregation of β-amyloid peptide aggregates with Clioquinol.
Figure 2:
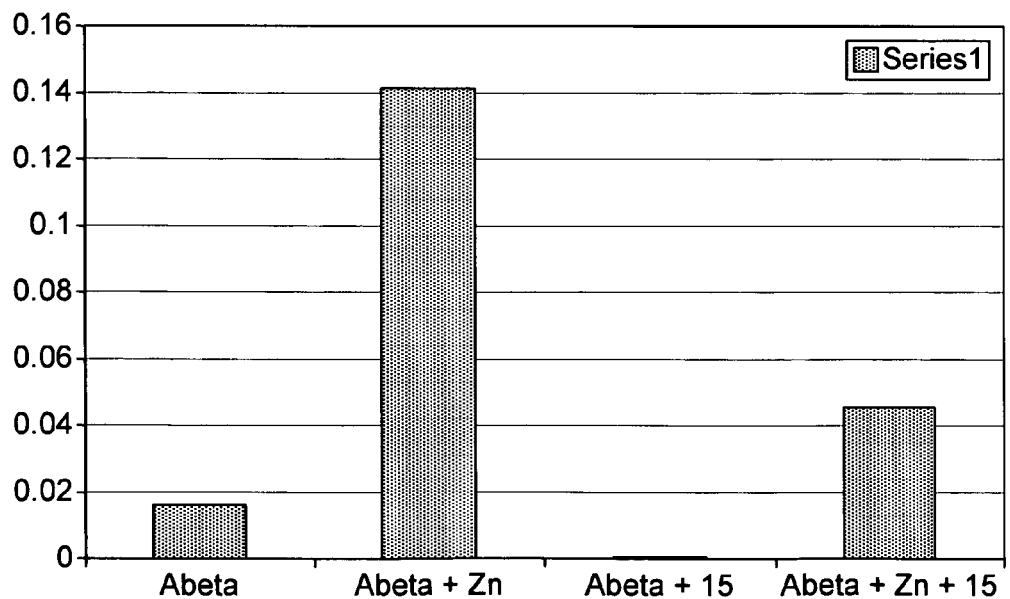
FIG. 2 Shows the disaggregation of β-amyloid peptide aggregates with compound 15.
Figure 3:
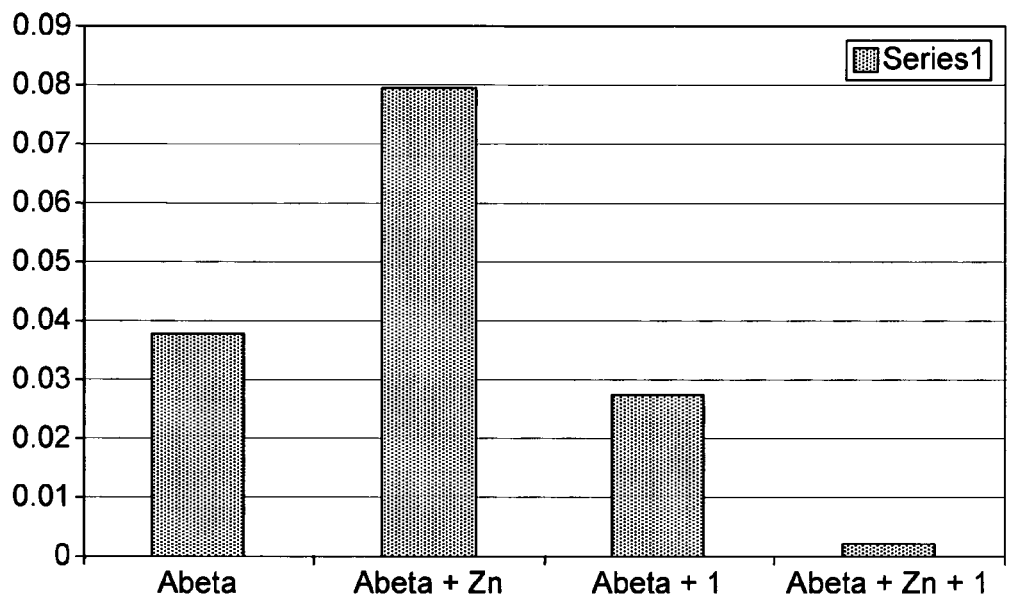
FIG. 3 Shows the disaggregation of β-amyloid peptide aggregates with compound 1.
Figure 4:
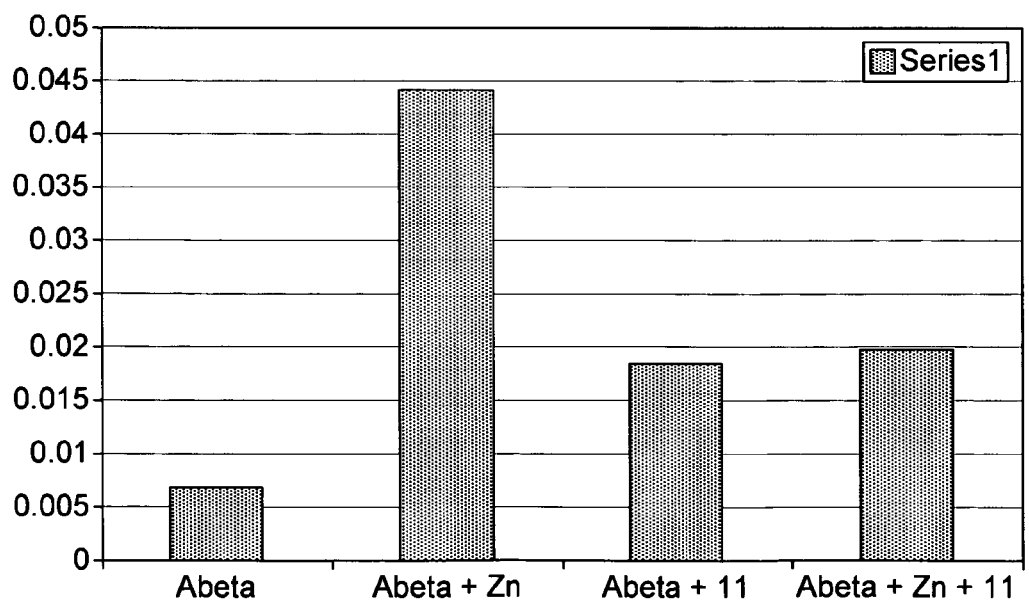
FIG. 4 Shows the disaggregation of β-amyloid peptide aggregates with compound 11.
Figure 5:
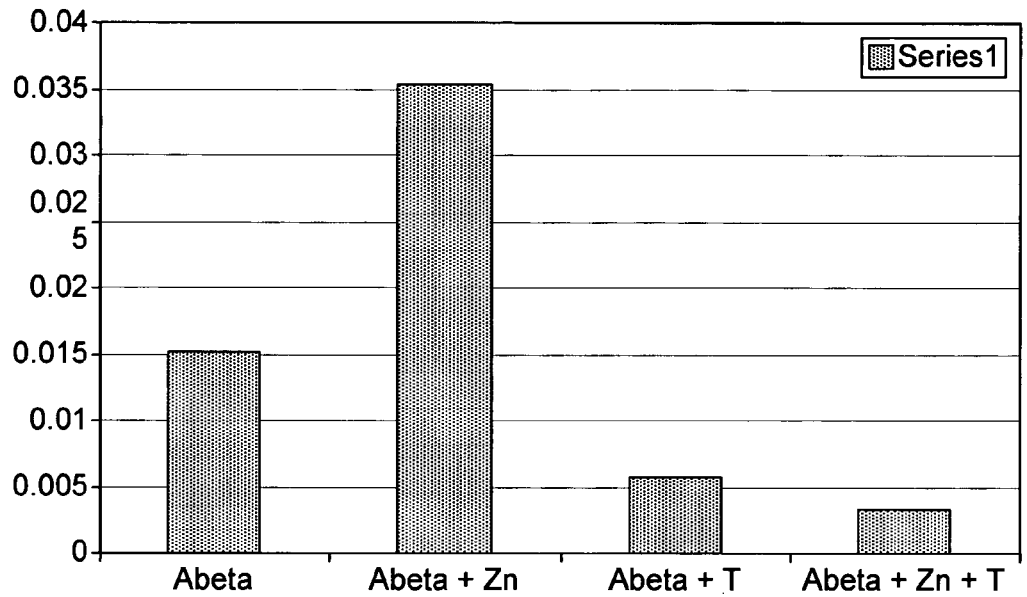
FIG. 5 Shows the disaggregation of β-amyloid peptide aggregates with compound mixture T.

FIG. 19 Images of brain tissue after post treatment with compounds 11, T, 21 and clioquinol.

EXAMPLES

The compounds promote disaggregation of zinc promoted accumulations of amyloidic deposits in vitro and reduce amyloidic load in H4 cellular models. They show no overt cellular or in vitro toxicity and reduce the plaque load in APP/Tau transgenic mice. The parenchymal zinc load is reduced in treated CD1 albino male mice. The body of evidence supports the claims that these compounds may be effective therapeutic agents in neurodegenerative disease states with amyloid or zinc based pathologies.

Compound Synthesis:

The following compounds were synthesized and stored in 1 mM stock solutions in DMSO or ethanol, as previously described in WO2004/101579.

Diethyl 7-oxomethylphosphonate-4-methylcoumarin (compound 1)

Ethyl 7-oxymethylphosphonic acid-4-methylcoumarin (compound 2)

4-Methyl-7-oxymethylphosphonic acid coumarin (compound 3)

Diethyl 5-indolyloxy methylphosphonate (compound 11)

The corresponding phosphonic acid ($\delta_P$ (109.7 MHz, DMSO) 16.2) is obtained as described.

Diethyl 4-(2-benzoxazolyl)phenoxymethylphosphonate (compound 12)
Diethyl 2-(2-benzoxazolyl)phenoxymethylphosphonate (compound 13)

The corresponding phosphonic acid $\partial_P$ (109.3 MHz, DMSO) 15.06 is obtained as described.

Diethyl 8-quinolyloxy methylphosphonate (compound 15)
Disodium 8-quinolyloxy methylphosphonate (compound 16)
Diethyl-2-carbazolyloxymethylphosphonate (compound 17)
2-carbazolyloxymethyl phosphonic acid (compound 18)
Diethyl N-carbazolylmethyl phosphonate (compound 19)
Disodium N-carbazolylmethylphosphonate (compound 20)
Diethyl(9-anthracyl N-butylaminemethylphosphonate (compound 21)
Diethyl N-(tert-butoxycarbonyl)-L-tyrosyl methyl ester methylphosphonate (compound 22)
Diethyl(9-anthracyl)-N-benzylaminemethylphosphonate (compound 23)
Diethyl(9-anthracyl)-N-butylaminemethylphosphonate (compound 24)
Diethyl 4-acetamidophenoxy methylphosphonate (compound 25)
Diethyl N-acridonyloxymethyl phosphonate (compound 26)

Compounds 27 and 28 may be obtained in the manner described for 26 from fluorescein and hydroxy pyrazole reagents.

Novel Compounds

Example 1

Compound 4

Diethyl 2-oxo-benzoxazolyl-3-methylphosphonic acid diethyl ester

A solution of 2-hydroxy-benzoxazole (2.7 g, 20 mmol) in dimethyl sulfoxide (15 ml) was added to sodium hydride (60%, 0.83 g, 21 mmol, washed with hexane) and left to stir for 1 h under nitrogen after the initial reaction had subsided. Diethyl 4-chlorophenylsulfonyloxy methylphosphonate (7.2 g, 21 mmol) dissolved in dimethyl sulfoxide (30 ml) was added and the solution was left to stir for 96 h at room temperature. The reaction mixture was poured into water (50 ml), and then extracted with ethyl acetate (2×75 ml). The combined organic extract was washed with brine dried over magnesium sulfate and concentrated under reduced pressure. The resultant oil was passed down a silica gel column using pet.ether:ethyl acetate (7:3) followed by 5% methanol in ethyl acetate:pet ether (8:2) an oil (4.1 g);
High Resolution Mass Spec. Found: 286.0837, $C_{12}H_{16}NO_5P$ (M+H)$^+$ requires 286.0839, $\delta_H$ (270 MHz, CDCl$_3$) 7.15 (4H, m), 4.17 (2H, d, J 10 Hz), 4.15 (4H, dq, J 6.8 Hz), 1.3 (6H, t, J 6 Hz), $\delta_P$ (109.3 MHz, CDCl$_3$) 18.9
Infra red ν (cm$^{-1}$) 1770 (s)
The corresponding phosphonic acid ($\delta_P$ 14.8) is obtained as described in WO2004/101579.

Example 2

Compound 5a

Diethyl 2-benzoxazolyl thiomethylphosphonate

A solution of 2-mercaptobenzoxazole (3.02 g, 20 mmol) in dimethyl sulfoxide (15 ml) was added to sodium hydride (60%, 0.83 g, 21 mmol, washed with hexane) and left to stir for 1 h under nitrogen after the initial reaction had subsided. Diethyl 4-chlorophenylsulfonyloxy methylphosphonate (7.2 g, 21 mmol) dissolved in dimethyl sulfoxide (30 ml) was added and the solution was left to stir for 96 h at room temperature. The reaction mixture was poured into water (50 ml), and then extracted with ethyl acetate (2×75 ml). The combined organic extract was washed with brine dried over magnesium sulfate and concentrated under reduced pressure. The resultant oil was passed down a silica gel column using first pet.ether:ethyl acetate (7:3) and then with 5% methanol in ethyl acetate:pet ether (8:2). The combined fractions from the second elution were subjected to further column chromatography using pet.ether:ethyl acetate 8:2 to give diethyl (2-benzoxazolyl) thiomethylphosphonate (2.5 g, 40%) as an oil. High Resolution Mass Spec. Found: 302.0608, $C_{12}H_{16}NO_4PS$ M$^+$+H requires 302.0610, $\delta_H$ (270 MHz, CDCl$_3$) 7.58 (1H, d, J 10 Hz), 7.44 (1H, d, J 10 Hz), 7.3 (2H, m), 4.12 (4H, dq, J 6.8 Hz), 3.65 (2H, d, J 13 Hz), 1.3 (6H, dt, J 6 Hz), $\delta_P$ (109.3 MHz, CDCl$_3$) 21.44,
The corresponding phosphonic acid ($\delta_P$ 19.31) is obtained as described in WO2004/101579.

Example 3

Compound 6

Diethyl 2-oxo-benzthiazolyl-3-methylphosphonic acid diethyl ester

A solution of 2-hydroxybenzthiazole (3.0 g, 20 mmol) in dimethyl sulfoxide (15 ml) was added to sodium hydride (60%, 0.83 g, 21 mmol, washed with hexane) and left to stir for 1 h under nitrogen after the initial reaction had subsided. Diethyl 4-chlorophenylsulfonyloxy methylphosphonate (7.2 g, 21 mmol) dissolved in dimethyl sulfoxide (30 ml) was added and the yellow solution was left to stir for 96 h at room temperature. The reaction mixture was poured into water (50 ml), and then extracted with ethyl acetate (2×75 ml). The combined organic extract was washed with brine dried over magnesium sulfate and concentrated under reduced pressure. The resultant oil was passed down a silica gel column using first pet.ether:ethyl acetate (7:3) to elute traces of starting materials and then ethyl acetate:pet.ether (9:1) and finally 10% MeOH in ethyl acetate to give diethyl 2-benzthiazolyl oxymethylphosphonate (2.5 g, 42%) as an oil.
High Resolution Mass Spec. Found: 302.0610, $C_{12}H_{16}NO_4PS$ (M+H)$^+$ requires 302.0607, $\delta_H$ (270 MHz, CDCl$_3$) 7.7 (1H, dd), 7.38 (1H, d), 7.25 (1H, m), 7.13 (1H, t), 4.34 (2H, d, J 11 Hz), 4.15 (4H, m), 1.25 (6H, t, J 7 Hz), $\delta_P$ (109.3 MHz, CDCl$_3$) 19.02
Infra red ν (cm$^{-1}$) 1685 (s)
The corresponding phosphonic acid $\delta_P$ (109.3 MHz, DMSO) 14.87 is obtained as described in WO2004/101579.

Example 4

Compound 7a

Diethyl 2-benzthiazolyl thiomethylphosphonate

A solution of 2-mercaptobenzthiazole (3.35 g, 20 mmol) in dimethyl sulfoxide (15 ml) was added to sodium hydride (60%, 0.83 g, 21 mmol, washed with hexane) and left to stir for 1 h under nitrogen after the initial reaction had subsided. Diethyl 4-chlorophenylsulfonyloxy methylphosphonate (7.2 g, 21 mmol) dissolved in dimethyl sulfoxide (30 ml) was added and the solution was left to stir for 96 h at room temperature. The reaction mixture was poured into water (50 ml), and then extracted with ethyl acetate (2×75 ml). The combined organic extract was washed with brine dried over magnesium sulfate and concentrated under reduced pressure. The resultant oil was passed down a silica gel column using first pet.ether:ethyl acetate (6:4) to elute traces of starting materials and then with 10% methanol in ethyl acetate (8:2) to elute products to give diethyl 2-benzthiazolyl thiomethylphosphonate (4.3 g, 68%) as an oil.

High Resolution Mass Spec. Found: 318.0381, $C_{12}H_{16}NO_3PS_2$ (M+H)$^+$ requires 318.0382, $\delta_H$ (270 MHz, CDCl$_3$) 7.85 (1H, d, J 7.5 Hz), 7.75 (1H, d, J 7.5 Hz), 7.4 (1H, t, J 7.5 Hz), 7.29 (1H, t, J 7.5 Hz), 4.15 (4H, dq, J 6.4 Hz), 3.79 (2H, d, J 16 Hz), 1.28 (6H, t, J 7.5 Hz), $\delta_P$ (109.3 MHz, CDCl$_3$) 22.13.

2-benzthiazolyl thiomethylphosphonic acid

To a stirred solution of diethyl 2-benzthiazolyl thiomethylphosphonate (0.2 g, 0.63 mmol) dissolved in dry dichloromethane (3.3 ml) under an atmosphere of nitrogen was added trimethylsilyl iodide (0.36 ml). The red solution was stirred for 2 h then methanol (5.1 ml) was added. After 2 h the solvent was removed under reduced pressure and then water (20 ml) was added to the residue. The mixture was concentrated under reduced pressure. Water (2 ml) was added and the mixture was concentrated under reduced pressure. This was repeated four times. The residue was washed finally with water then acetone to give 2-benzthiazolyl thiomethylphosphonic acid (0.06 g, 36%), $\delta_P$ (109.3 MHz, DMSO) 15.49; $\delta_H$ (270 MHz, DMSO) 8.05 (1H, d, J 7.5 Hz), 7.75 (1H, d, J 7.5 Hz), 7.5 (1H, t, J 7.5 Hz), 7.35 (1H, t, J 7.5 Hz), 3.6 (2H, d, J 16 Hz)

Example 5

Phosphonomethylation of 2-hydroxybenzimidazole

A solution of 2-hydroxybenzimidazole (2.68 g, 20 mmol) in dimethyl sulfoxide (15 ml) was added to sodium hydride (60%, 0.83 g, 21 mmol, washed with hexane) and left to stir for 1 h under nitrogen after the initial reaction had subsided. Diethyl 4-chlorophenylsulfonyloxy methylphosphonate (7.2 g, 21 mmol) dissolved in dimethyl sulfoxide (30 ml) was added and the solution was left to stir for 96 h at room temperature. The reaction mixture was poured into water (50 ml), and then extracted with ethyl acetate (2×75 ml). The combined organic extract was washed with brine dried over magnesium sulfate and concentrated under reduced pressure. The resultant oil was passed down a silica gel column using first pet.ether:ethyl acetate (1:1), then: ethyl acetate:pet.ether (9:1) and finally ethyl acetate:pet.ether (9:1) with 5% methanol. The compounds 8, 8a and 10 below were obtained:

2-oxo-benzimidazolyl-3-dimethylphosphonic acid diethyl ester (compound 8)

Mass Spec (CI). Found: 284.9, $C_{12}H_{17}O_4N_2P$ (M+H)$^+$ requires 285.2; $\delta_H$ (270 MHz, CDCl$_3$) 7.4 (4H, m, J$_1$ 12 Hz, J$_2$ 6 Hz, J$_3$ 4 Hz), 4.28 (2H, d, J 10.8 Hz), 4.15 (4H, qq, J 5 Hz), 1.25 (6H, t, J 8 Hz); $\delta_P$ (109.3 MHz, CDCl$_3$) 20.4. Structure confirmed by single crystal XRD.

2-oxo-benzimidazolyl-3,3'-bis-methylphosphonic acid diethyl ester (compound 10)

High Resolution Mass Spec. Found: 435.1446, $C_{17}H_{29}O_7N_2P_2$ M$^+$+H requires 435.1445; $\delta_H$ (270 MHz, CDCl$_3$) 7.4 (4H, m, J$_1$ 12 Hz, J$_2$ 6 Hz, J$_3$ 4 Hz), 4.26 (4H, d, J 10.5 Hz), 4.15 (8H, qq, J 5 Hz), 1.25 (12H, t, J 8 Hz); $\delta_P$ (109.3 MHz, CDCl$_3$) 20.2

Diethyl 2-benzimidazolyloxymethylphosphonate (compound 8a)

$\delta_H$ (270 MHz, CDCl$_3$) 7.4 (4H, m, J$_1$ 12 Hz, J$_2$ 6 Hz, J$_3$ 4 Hz), 4.12 (2H, d, J 8 Hz), 3.9 (4H, dq, J 5 Hz), 1.15 (6H, t, J 8 Hz); $\delta_P$ (109.3 MHz, CDCl$_3$) 20.6; Isolated from a reaction similar to that above except that the 2-hydroxybenzimidazole was treated with potassium carbonate instead of sodium hydride.

Example 6

Compound 14

Diethyl 2-(2-benzthiazolyl)phenoxymethylphosphonate

To sodium hydride (60%, 0.83 g, 21 mmol, washed with dry hexane) was added dropwise, with stirring under nitrogen, 2-(2-benzthiazolyl)phenol (4.54 g, 20 mmol) in dimethyl sulfoxide (15 ml). After a further 1 h stirring at 80° C. diethyl 4-chlorophenylsulfonyloxy methylphosphonate (7.2 g, 21 mmol) dissolved in dimethyl sulfoxide (30 ml) was added and the solution was stirred for a further 96 h at 80° C. The reaction mixture was treated with water (50 ml) and then extracted with ethyl acetate (3×50 ml). The combined organic extracts were washed with brine and then dried. Evaporation of the solvent left an oily solid that on elution from silica, first with pet. ether-ethyl acetate (4:6) to remove traces of starting materials, then pet. ether-ethyl acetate (3:7) and finally ethyl acetate gave diethyl 2-(2-benzoxazolyl)phenoxymethylphosphonate as an oil $\delta_H$ (270 MHz, DMSO) 8.42 (1H, d, J 7.7 Hz), 8.11 (1H, d, J 7.7 Hz), 8.04 (1H, d, J 7.7 Hz), 7.53 (2H, m), 7.32 (2H, m), 7.42 (2H, m), 7.21 (1H, t, J 7.7 Hz), 4.73 (2H, d, J 10.5 Hz), 4.18 (4H, dq, J$_1$ 6.7 Hz) and 1.28 (6H, t, J 7 Hz), $\delta_P$ (109.7 MHz, DMSO) 19.72

$\delta_H$ (270 MHz, CDCl$_3$) 8.52 (1H, d, J 7.7 Hz), 8.1 (1H, d, J 7.7 Hz), 8.04 (1H, d, J 7.7 Hz), 7.48 (2H, q, J 7.7 Hz), 7.36 (H, t, J 7.7 Hz), 7.14 (1H, t, J 7.7 Hz), 4.5 (2H, d, J 10 Hz), 4.25 (4H, dq, J$_1$ 7 Hz) and 1.35 (6H, t, J 7 Hz), $\delta_P$ (109.7 MHz, CDCl$_3$) 18.9

High Resolution Mass Spec. Found: 378.0925, $C_{18}H_{20}NO_4P$ (M+H)$^+$ requires 378.0923, 2-(2-benzthiazolyl)phenoxymethylphosphonic acid To a stirred solution of diethyl 2-(2-benzthiazolyl)phenoxymethylphosphonate (0.2 g, 0.53 mmol) dissolved in dry dichloromethane (2.7 ml) under an atmosphere of nitrogen was added trimethylsilyl iodide (0.31 ml). The red solution was stirred for 2 h then methanol (4.3 ml) was added. After 2 h the solvent was removed under reduced pressure and then water (3.5 ml) was added to the residue. The mixture was concentrated under reduced pressure. Water (2 ml) was added and the mixture was concentrated under reduced pressure. This was repeated four times. The residue was washed finally with water then acetone to give 2-(2-benzthiazolyl)phenoxymethylphosphonic acid (0.13 g, 77%) $\delta_H$ (270 MHz, DMSO) 8.43 (1H, d, J 8 Hz), 8.04 (2H, m), 7.53 (2H, m), 7.44 (2H, m), 7.21 (1H, t, J 8 Hz), 4.4 (2H, d, J 12 Hz), $\delta_P$ (109.7 MHz, DMSO) 14.4

Biological Activity of Compounds According to the Invention

Compound Testing Regimes

Example 7

β-amyloid peptide was aggregated in vitro in the presence of Zn, and the formation of aggregates was assessed in the presence or absence of the substituted phosphonates. The method used to assess effects on aggregation was based on a turbidimetry assay, as previously described in literature (Klug et al., 2003; Qahwash et al., 2003). Aβ1-40 (25 μM) was incubated for 48 h in the absence or presence of zinc (100 μM). Substituted phosphonates (1 μM) were added at the beginning of the incubation. The tests were conducted in multiwell culture plates, and the plates gently shaken during incubation. After 48 h, absorbance was measured at 405 nm using an ELISA plate reader. Clioquinol (1 μM) was used as a reference compound.

Compounds proposed for therapeutic treatment of amyloidopathy related disease states such as AD possess the ability the dissagregate zinc or copper aggregated amyloid in vitro as a first indicator of therapeutic potential. Using a turbidimetry-based approach (FIGS. 1-5), and clioquinol (1 μM) as the reference compound substantial disaggregation, presented as average % inhibition of aggregation in the presence of Zn, was seen for the substituted phosphonates shown in FIGS. 1-5 as well as several other phosphonates shown in the Table in the form of their di sodium phosphonate derivatives instead of ethyl ester derivatives.

Example 8

A first assessment of the potential toxicity of the substituted phosphonates was carried out in a non-neuronal cell line, using a tetrazolium salt (MTT) colorimetric assay, based on the method described by Mossman (1983), which gives a reflection of mitochondrial activity and cell integrity. The MTT [3-(4,5-dimethylthiazol-2-yl)-2,5-diphenyltetrazolium bromide] assay is based on the ability of a mitochondrial dehydrogenase enzyme from viable cells to cleave the tetrazolium rings of the pale yellow MTT and form dark blue formazan crystals which cannot cross cell membranes. The result is that healthy cells will accumulate more of the blue formazan crystals. Solubilisation of the cells by the addition of a detergent results in the liberation of the crystals. The number of surviving cells is directly proportional to the level of the formazan product created. Using the L929 immortalised fibroblast cell line, cells were seeded into a multiwell culture plate and were exposed to increasing concentrations of metal-chelating compounds (0.3 nM to 1 μM) for 30 minutes, 4 hours and 24 hours. They were then incubated for 2 h after addition of MTT (1 mg/ml) and the absorbance was read at 570 nm. Control wells were incubated either in the presence of culture medium, or in the presence of culture medium to which ethanol or DMSO was added, at the highest concentration used in the experiment (corresponding to the 1 μM concentration of substituted phosphonates). The toxicity of the reference compound clioquinol (0.3 nM to 1 μM) was assessed under the same conditions, for comparison.

Compounds proposed for in vivo therapeutic treatments should not display overt toxicity.

Figure 6:
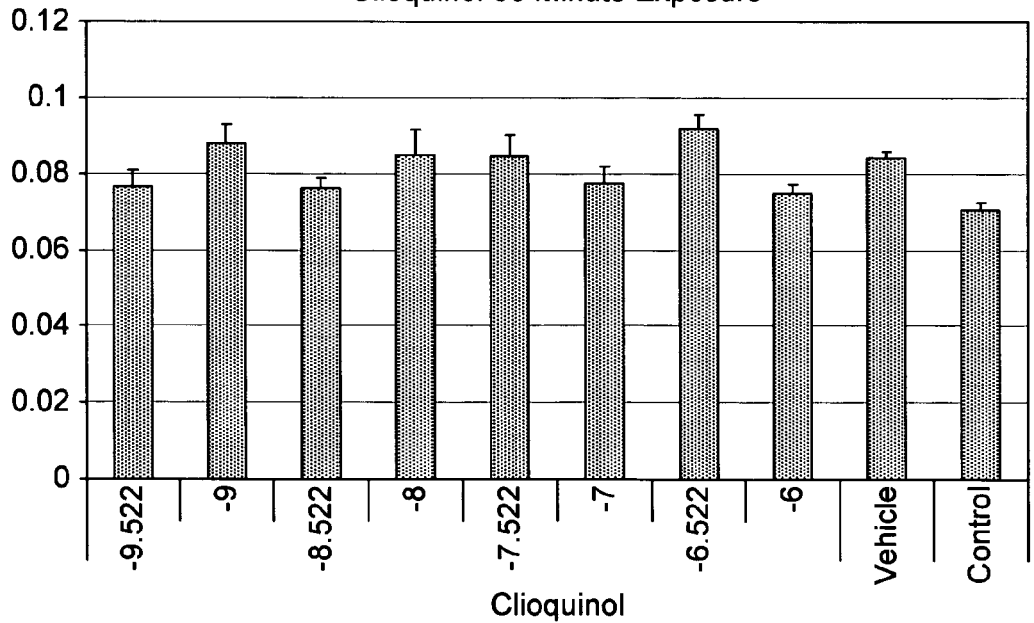
FIG. 6 Shows L929 non-neural cell line viability with clioquinol to determine toxicity.
Figure 7:
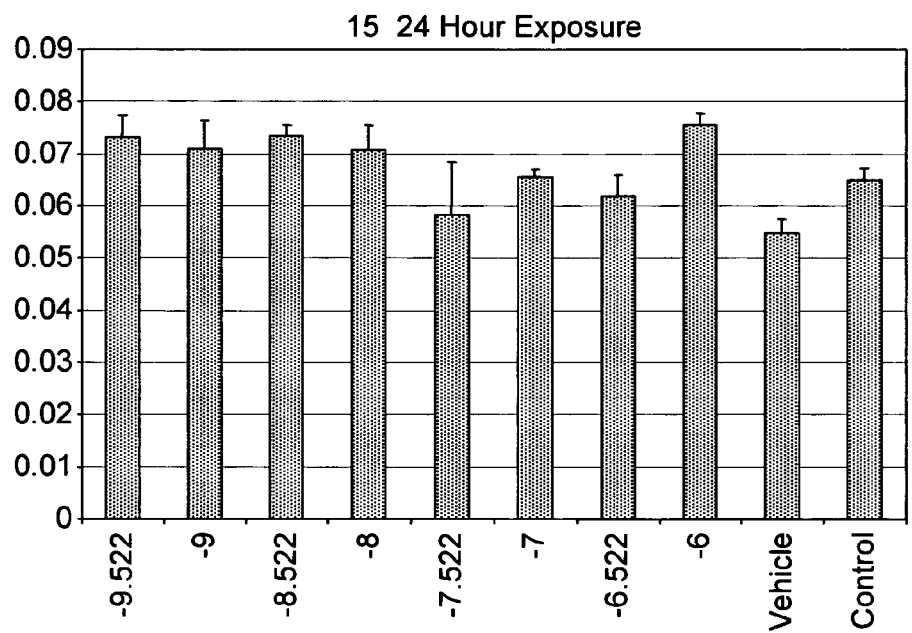
FIG. 7 Shows L929 non-neural cell line viability with compound 15 to determine toxicity. H4 cell survival and amyloid accumulation (expressed as the average value of 2-3 separate experiments) is shown for all the primary compounds at 1 µM.
Figure 8:
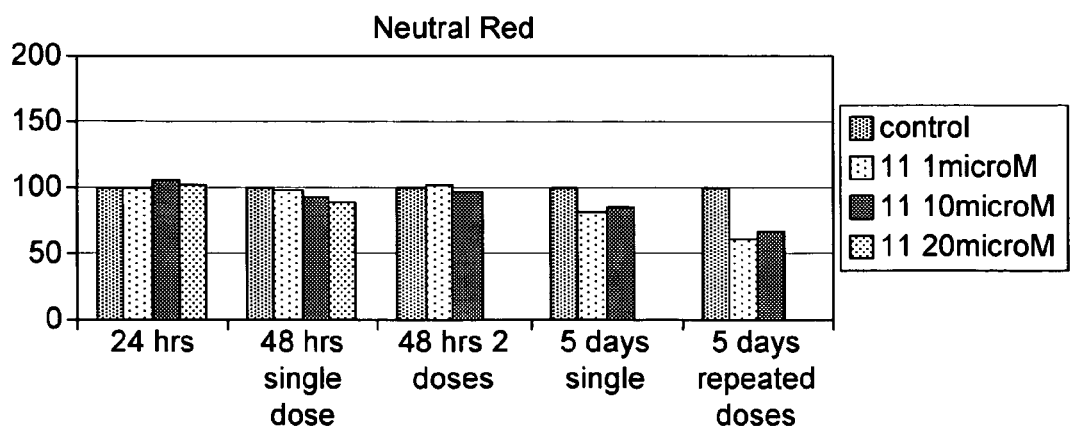
FIG. 8 Shows human neuroblastoma cell line H4 cell viability with compound 11 using Neutral Red.
Figure 11:
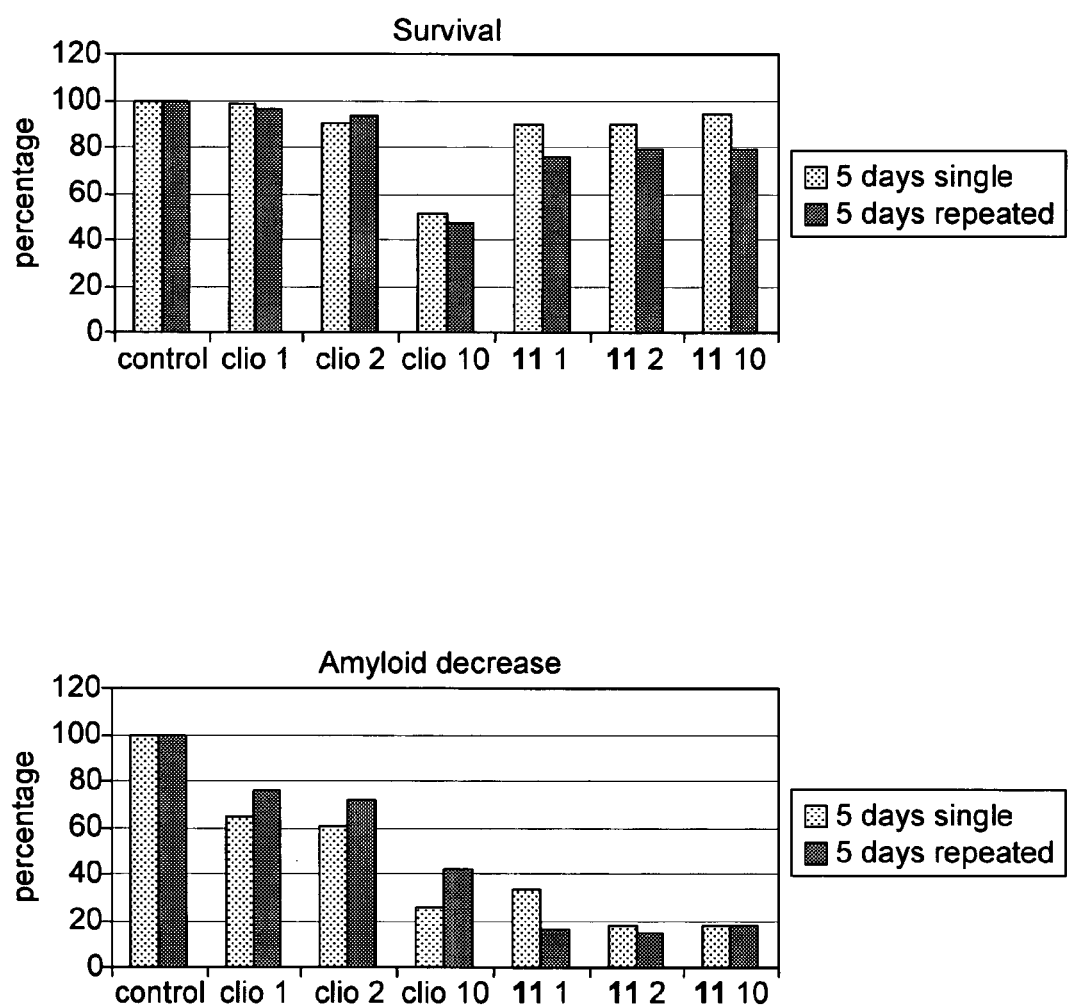
FIG. 11 Shows human neuroblastoma cell line cell viability/survival and amyloid accumulation data for compound 11.
Figure 12:
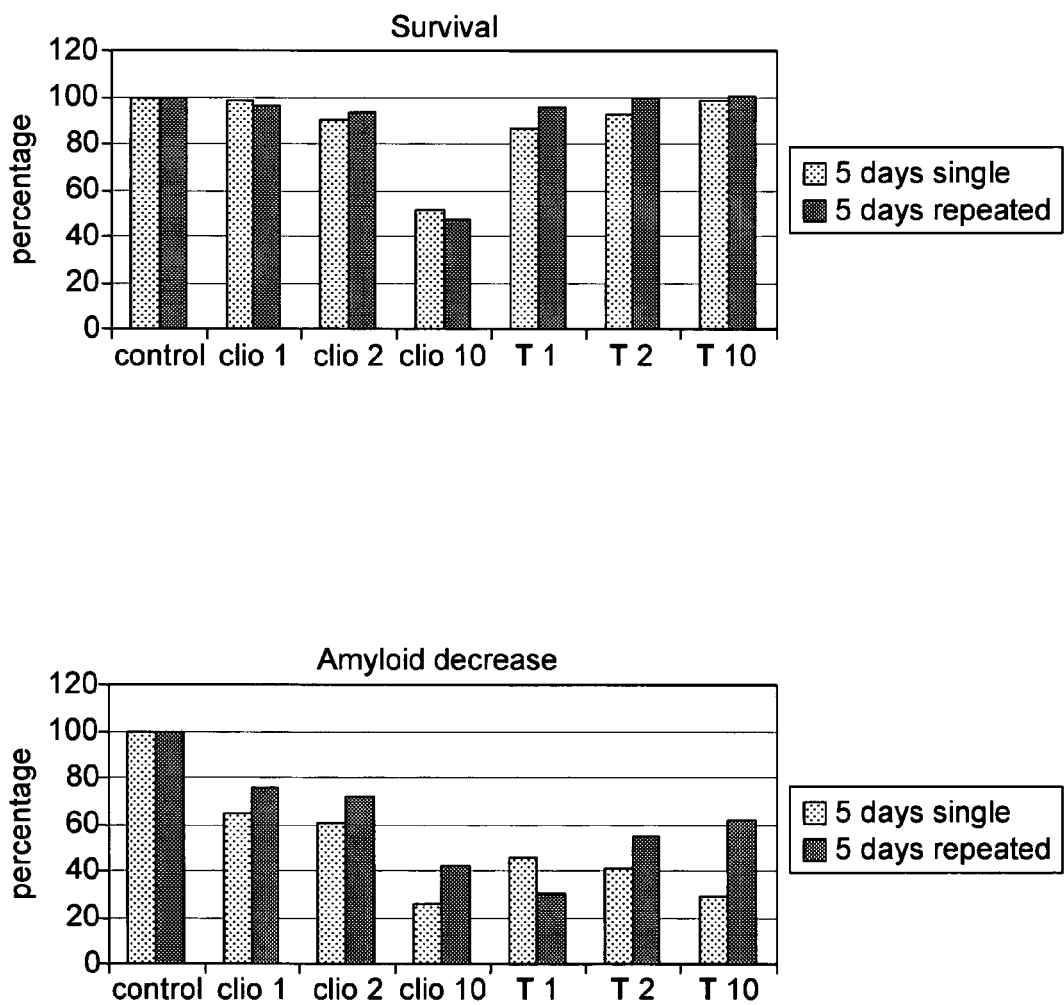
FIG. 12 Shows human neuroblastoma cell line cell viability/survival and amyloid accumulation data for compound T.
Figure 13:
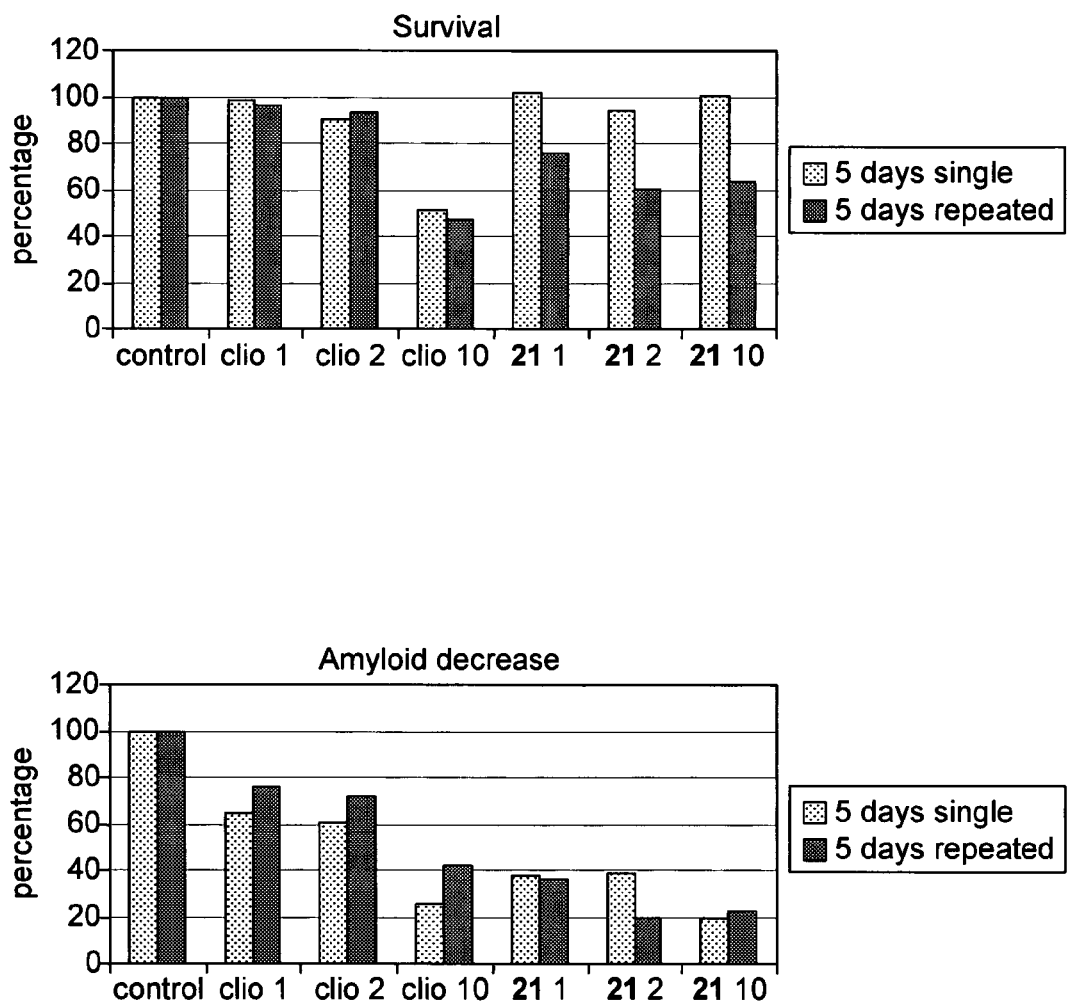
FIG. 13 Shows human neuroblastoma cell line cell viability/survival and amyloid accumulation data for compound 21.
Figure 14:
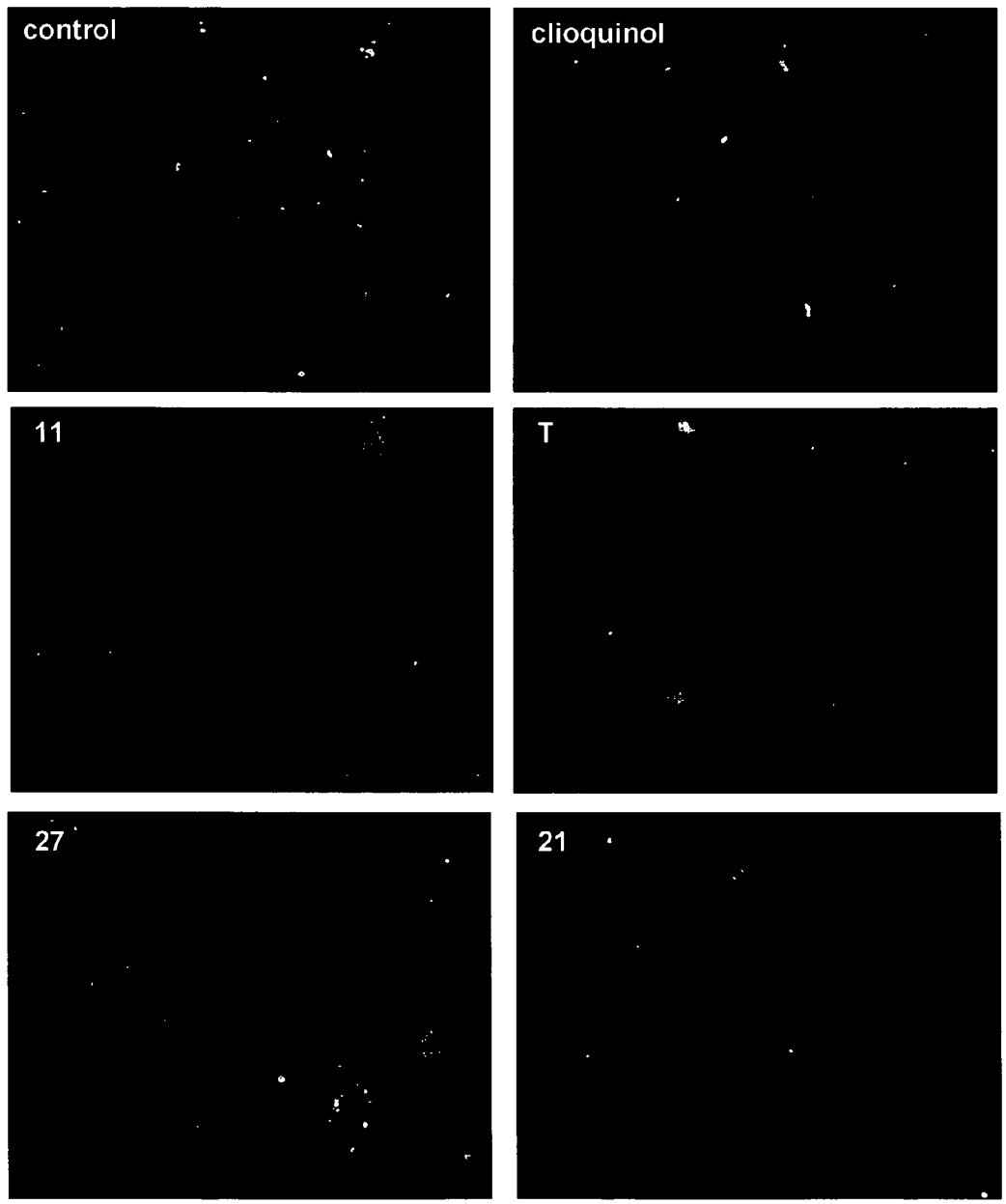
FIG. 14 Shows the intracellular distribution of amyloid in human neuroblastoma cell line H4 cells after incubation with compounds 11, 27, 21, T and clioquinol.

A first assessment of toxicity of the substituted phosphonates was carried out in a non-neuronal cell line, using a tetrazolium salt (MTT) colorimetric assay, based on the method described by Mossman (1983), which gives a reflection of mitochondrial activity and cell integrity (FIGS. 6 and 7). The toxicity of the reference compound clioquinol (0.3 nM to 1 μM) was assessed under the same conditions, for comparison.

The analysis of cell viability using the MTT assay, shows that under the conditions used, neither clioquinol nor any of the substituted phosphonates screened showed any toxicity, as reflected in cell viability after up to 24 h exposure to compounds over a wide range of concentrations.

Example 9

H4 cells (human neuroblastoma cell line) were used to test the ability of the substituted phosphonates to disrupt amyloid accumulation. Parallel 96 well plates were also set up with the H4 cells to assess the effect of the compounds on cell survival. Clioquinol was used as the reference compound. All tested compounds were made up in the growth media at the following concentrations: 1 μM, 2 μM and 10 μM. The compounds were initially tested over 48 hours either with a single dose of the compound or with 2 doses. This was extended to a 5 day period again, either with a single dose of the compound or with repeated daily doses of the compounds.

Cell Survival

For the cell survival, two cell viability/toxicity assays were used: the assay based on MTT (described above), and an assay based on the use of neutral red (NR).

The MTT assay was carried out at the end of the culture periods using the standard protocol described above for the fibroblast cell line, and the absorbance read on a microplate reader.

The Neutral Red (NR) cytotoxicity assay procedure also measures cell survival/viability. It is based on the ability of cells to incorporate and bind NR, a supravital dye. Alterations of the cell surface or of the sensitive lysosomal membrane lead to lysosomal fragility, which results in the cells becoming unable to bind the NR dye. The NR assay was compared to the MTT cytotoxity assay. Both assays yielded comparable data but as the optical density values with the NR assay were about twice that obtained with the MTT assay, this provided us with a more sensitive test and required fewer cells for analysis. It also allowed to check that the compounds did not have a direct effect on the lysosomes or interfere with mitochondrial enzymes which would have resulted in greater toxicity in the NR vs. the MTT assays, respectively.

Cells were grown and once they reached the desired density, they were rinsed with phosphate-buffered saline and 200 μl of NR-containing medium (40 μg/ml) was added to each well and cells were incubated with the dye for 3 hrs. The NR medium was removed and the cells washed with 200 μl phosphate-buffered saline (PBS). 200 μl of an acetic acid/ethanol mixture (1 ml glacial acetic acid in 100 ml 50% ethanol) was used to desorb the NR for 15 min at room temperature. The plate was then placed on a shaker at 60 rpm for 30 min to form a homogenous solution. The absorbance was measured at 540 nm in a microplate reader, using the blank as a reference.

Amyloid Accumulation

For the amyloid accumulation the cells were fixed with ice cold methanol for 3 minutes then washed with PBS 3 times 3 minutes. The 6E10 antibody (Abcam 1:5,000) was added and the cells incubated for 48 hours at 4° C. The primary antibody was removed and the cells washed with PBS 3 times 3 minutes, and the secondary antibody (anti-mouse HRP 1:4,000) was added for 2 hours. This was removed and the cells washed 3 times 3 minutes. They were then incubated with the OPD substrate (prepared according to the manufacturer's instructions) for 30 min, before reading the absorbance.

All 5 day experiments were repeated 3 times to confirm results, and all 48 hour studies were repeated twice.

In a further assessment of the compounds for toxicity and ability to modulate amyloidopathic pathways in vitro they were screened using H4 cells (human neuroblastoma cell line) (FIGS. 8-15 and Tables 1a and 2a). For the cell survival, two cell viability/toxicity assays were used: the assay based on MTT (described above), and an assay based on the use of NR. Clioquinol was used as the reference compound.

A summary of the H4 cell survival and amyloid accumulation (expressed as the average value of 2-3 separate experiments) is shown for all the primary compounds at 1 µM in Tables 1a and 2a, with the control cells grown in growth media (with the corresponding trace amounts of DMSO or ethanol added) representing the 100% value. The cell survival of the H4 cells assayed with either MTT or NR were comparable, and the graphs show the NR assay results only.

Clioquinol at 1 µM with a single dose or a repeated dose over the 5 day period has no toxicity, and decreases the accumulation of amyloid (Table 1a and Table 2a). In contrast, clioquinol leads to decreased cell survival at the 2 µM concentration, and there is extensive death of the H4 cells at the 10 µM concentration, either with a single dose or repeated doses of the drug.

As shown in Table 1a, the substituted phosphonates appear to be devoid of toxicity upon single exposure for 5 days to 1 µM. Repeated doses reduce in some cases cell viability (maximum 28% reduction seen with the compound 20). The analysis of cell viability using the NR assay gave comparable results to those obtained with the MTT assay, as exemplified for the compound 11. The exposure to 11 for 5 days (single exposure) did not affect significantly cell survival, whereas after 5 days and repeated dose, the compound reduced cell viability to approximately 60-70% of the control value. Similarly, 1 did not affect viability after single exposure, but reduced it to 70-80% after 5 days repeated dose.

As illustrated in Table 2a, the effect of the substituted phosphonates on amyloid accumulation is striking, with a majority of the compounds outperforming the reference compound clioquinol, in terms of effects on amyloid accumulation, at the lowest concentration tested (1 µM). For example, for a 5 day single dose, the compounds 1 and 21 reduce the amyloid accumulation to 37% of the value of controls, whereas the reference compound clioquinol reduced the accumulation to 64% of the value in controls.

Table 1a Summary of cell survival (% controls)
Table 2a Summary of amyloid reduction (% controls)

H4 cell survival and amyloid accumulation (expressed as the average value of 2-3 separate experiments) is shown for all the primary compounds at 1 µm

TABLE 1a

Summary of cell survival (% controls)

|  | 5 day single dose | 5 day repeated doses |
|---|---|---|
| Control | 100 | 100 |
| clio 1 µM | 99 | 96 |
| 1 1 µM | 104 | 78 |
| 5 1 µM | 100 | 113 |
| 7 1 µM | 116 | 86 |
| T 1 µM | 87 | 97 |
| 11 1 µM | 90 | 76 |
| 14 1 µM | 100 | 110 |
| 15 1 µM | 89 | 95 |
| 17 1 µM | 97 | 102 |
| 20 1 µM | 88 | 72 |

TABLE 1a-continued

Summary of cell survival (% controls)

|  | 5 day single dose | 5 day repeated doses |
|---|---|---|
| 22 1 µM | 99 | 80 |
| 28 1 µM | 107 | 85 |
| 24 1 µM | 105 | 135 |
| 25 1 µM | 98 | 97 |
| 27 1 µM | 114 | 113 |
| 21 1 µM | 104 | 76 |
| 26 1 µM | 116 | 86 |

TABLE 2a

Summary of amyloid reduction (% controls)

|  | 5 day single dose | 5 day repeated doses |
|---|---|---|
| control | 100 | 100 |
| clio 1 µM | 64 | 76 |
| 1 1 µM | 37 | 19 |
| 5 1 µM | 38 | 74 |
| 7 1 µM | 92 | 63 |
| T 1 µM | 47 | 31 |
| 11 1 µM | 33 | 16 |
| 14 1 µM | 100 | 83 |
| 15 1 µM | 36 | 71 |
| 17 1 µM | 37 | 62 |
| 20 1 µM | 11 | 66 |
| 22 1 µM | 10 | 17 |
| 28 1 µM | 58 | 82 |
| 24 1 µM | 48 | 15 |
| 25 1 µM | 24 | 62 |
| 27 1 µM | 30 | 61 |
| 21 1 µM | 37 | 35 |
| 26 1 µM | 57 | 52 |

Example 10

Intracellular Distribution of Amyloid after Incubation

In separate experiments we also made observations with some of the compounds, on the intracellular distribution of amyloid in H4 cells. This was carried out by using the primary 6E10 antibody, followed by incubation of the cells with fluorescently-tagged secondary antibodies.

Under basal conditions, the intracellular labelling of amyloid in the H4 cells showed accumulations of peptides within the control cells throughout the cytoplasm of the cells. The addition of 1 µM clioquinol for 5 days reduced this intracellular accumulation in some of the cells, but brightly labelled areas could still be found. After addition of 1 µM of the compounds 11 and T, T=compounds 8 and 10 in 9:1 mole ratio, the number of cells with these brightly labelled amyloid accumulations was reduced (compared to cliquinol) but not entirely abolished. After incubation with 21, there were virtually no cells with these amyloid bright intracellular accumulations. The incubation with 27 (1 µM) also led to a reduction in the amyloid labelling in the H4 cells but there were still cells with bright labelling.

The figure shows H4 cells labelled for amyloid:control, clioquinol, 11, T, 27, and 21 treatment groups. Amyloid labelling was carried out after 5 days incubation of the cells with 1 µM compound (single dose).

A further indicator of potential therapeutic effect in amyloidiopathic pathways is determined by the effect on intracellular amyloid production.

In separate experiments we also made observations with some of the compounds, on the intracellular distribution of amyloid in H4 cells (FIG. 15). This was carried out by using the primary 6E10 antibody, followed by incubation of the cells with fluorescently-tagged secondary antibodies. Under basal conditions, the intracellular labelling of amyloid in the H4 cells showed accumulations of peptides within the control cells throughout the cytoplasm of the cells. The addition of 1 µM clioquinol for 5 days reduced this intracellular accumulation in some of the cells, but brightly labelled areas could still be found. After addition of 1 µM of the compounds 11 and T, the number of cells with these brightly labelled amyloid accumulations was reduced (compared to clioquinol). After incubation with 21, there were virtually no cells with these amyloid bright intracellular accumulations. The incubation with 27 (1 µM) also led to a reduction in the amyloid labelling in the H4 cells. The FIG. 15 shows H4 cells labelled for amyloid:control, clioquinol, 11, T, 27, and 21 treatment groups. Amyloid labelling was carried out after 5 days incubation of the cells with 1 µM compound (single dose). 11, T, 26, 21. The compound 27 is a fluorescein compound and we were able to detect it in cells using its natural fluorescence. These data show that substituted phosphonates reduced the accumulation of amyloid in the H4 cell line, without marked reduction in cell survival. Furthermore, there was also a reduction in the extracellular accumulation of amyloid after incubation with some substituted phosphonates which suggests that these compounds may act both extra- and intracellularly to reduce the amyloid accumulation. Many of the substituted phosphonates described herein contain a fluorogenic component and using 27 as example this compound was visualised within the cell located proximal to the labelled amyloid. These data show that the natural fluorescence of the substituted phosphonates provides a means of visualising the compounds as they target cellular and in vitro acellular amyloidic deposits.

Example 11

Cultures of dorsal root ganglia neurones from adult Wistar rats were incubated with clioquinol and with selected substituted phosphonates (compounds 11, T, 21, 1) at 1 µM for 24 hours and 4 days, to assess the toxicity of the compounds. Briefly, the method used was as follows:

Adult male Wistar rats where sacrificed by $CO_2$ inhalation and the dorsal root ganglia from all segmental levels were removed and dissociated into cells. The total number of cells was counted using a haemocytometer and 500 cells plated onto pre-coated 8 well chambered slides. The cells were left to adhere for at least 6 hours before the addition of the test substituted phosphonates compounds or clioquinol to the media. Cells were grown for 1 day or 4 days and either had a single dose of the test compounds, or the media and compounds were changed every day over the 4 day period. Compounds were added at 1 µM and 10 µM concentrations, with duplicates of each concentration and each experiment repeated 4 times.

After 4 days the cells were fixed, then washed and incubated with primary antibody (anti-mouse beta tubulin III, Sigma, 1:1,000) for 24 hours at room temperature. The primary antibody was removed, the cells washed and then incubated with secondary antibody (donkey anti-mouse FITC labeled (Jackson 1:400)) for at least 2 hours at room temperature. The secondary antibody was removed, the cells washed and the slides were mounted with DABCO PBS:glycerol as an antifade. Analysis was done by counting all beta tubulin III positive cells in each well. Values were determined in triplicate and experiments were repeated 4 times (twice in case of 22).

Figure 16:
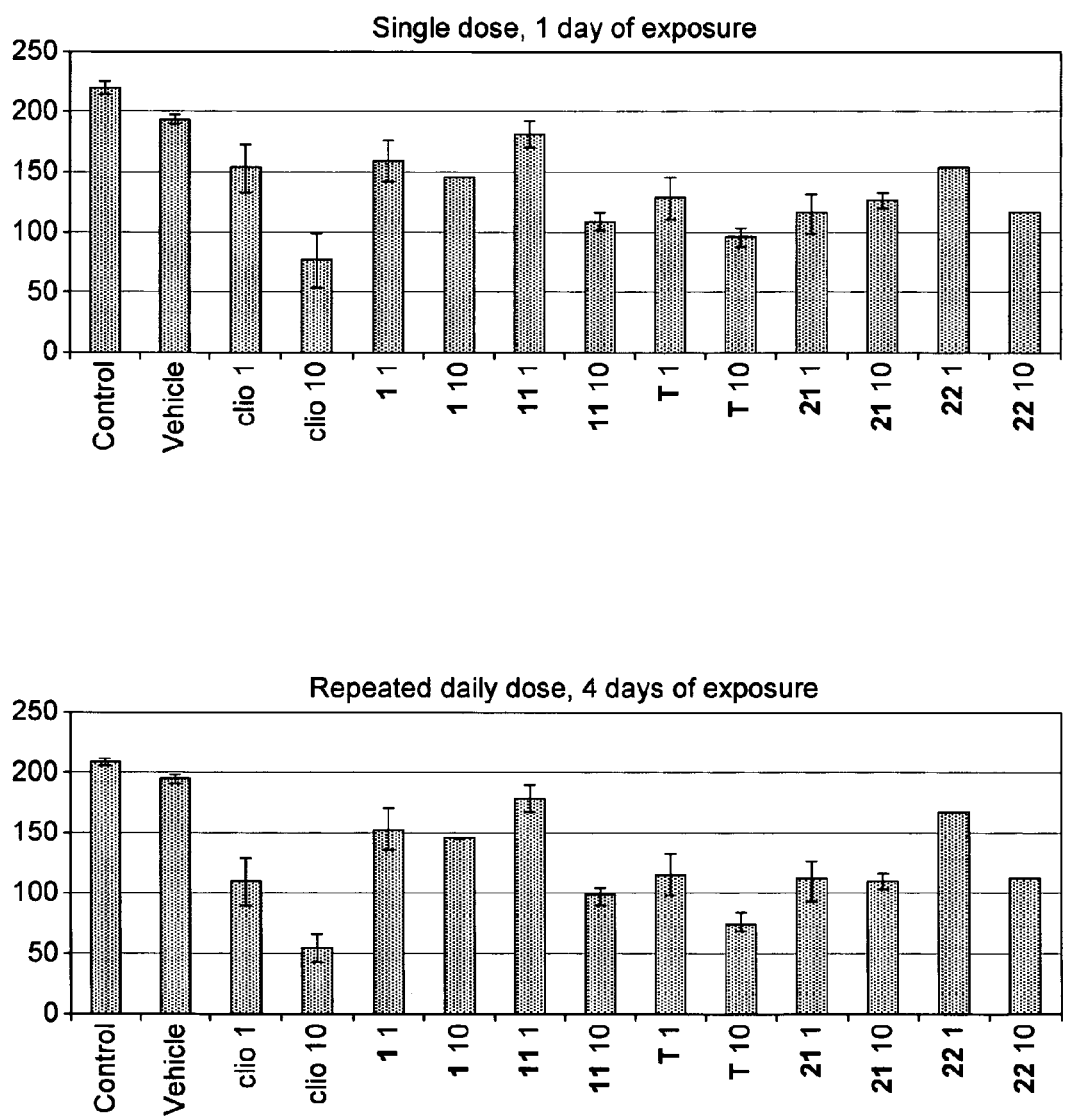
FIG. 16 Shows effects of compounds 1, 10, 11, T, 21, 22 and clioquinol on primary sensory neurons.

Lack of toxicity to neuronal cells is a prerequisite for therapeutics targeting neurodegenerative disease states such as AD so the effects of the substituted phosphonates on primary sensory neuron cultures were assessed for toxicity in relation to the adult nervous tissue (FIGS. 16 and 17).

A single dose of clioquinol or the substituted phosphonate compounds (1 or 10 microMolar) was given at the start of the culture period and the neurons were incubated for 1 day, or the daily dose was repeated and the cells were maintained for 4 days. Viability was considerably better for the substituted phosphonate compounds than for the clioquinol reference compound.

Example 12

CD1 albino male mice (18-20 g, Charles River, UK) were treated for 4 days with the following compound: clioquinol 30 mg/kg p.o., clioquinol 10 mg/kg i.p., and compounds 11, T, 21, 1 at 10 mg/kg, i.p. (or the vehicle used to dissolve the drugs for administration p.o. or i.p). On the $4^{th}$ day of administration of the compounds or of the respective vehicle, mice received 1 hour before clioquinol or the substituted phosphonates an i.p. injection of sodium selenite 10 mg/kg. All animals were killed by cervical dislocation 2.5 hours after the administration of sodium selenite. The brain was frozen on dry ice, and then 15 µm sections were cut and stained to reveal the distribution of zinc using an autometallographic technique based of exposure of the tissue to a silver reagent enhancement kit (Aurion) (Wang et al, 2001). Some sections were counterstained with toluidine blue.

For therapeutics targeting neurodegenerative disease states such as AD prerequisites include lack of any overt toxicity, ability to access the CNS (central nervous system) and to provide neuro protection as evidenced for example in AD by modulating the formation of zinc containing amyloid deposits. In a first aspect, the assessment of the effect of the systemic administration of the substituted phosphonates on zinc distribution in the CNS (which is a reflection of the penetration of the blood-brain barrier, BBB, by the compounds) and a preliminary assessment of systemic toxicity after semichronic administration in mice was undertaken (FIG. 18). All compounds tested were devoid of overt systemic toxicity using this administration paradigm, and no behavioural abnormalities were noted in animals receiving the new compounds. The autometallographic technique revealed the presence of an intense zinc signal in the brain of control animals, after administration of vehicle i.p. or vehicle p.o. (see images FIG. 18). The administration of benchmark clioquinol or substituted phosphonates led to variable degrees of decrease in the zinc staining in the central nervous system. Marked decreases were seen in the zinc signal after administration of clioquinol 10 mg/kg, i.p. Decreases in the zinc signal were seen after clioquinol 30 mg/kg p.o. or 11, T, 21, 1 at 10 mg/kg, i.p. The decreased zinc staining signal is strong evidence for the passage of cliquinol (i.p, or p.o.) and of the substituted phosphonates compounds across the BBB, and their ability to chelate zinc in this environment. The systemic i.p. administration of substituted phosphonates leads to decrease in the signal that reflects central zincergic pathways. This supports the bioavailability of the compounds and their ability to reduce zinc in the brain parenchyma.

Example 13

Transgenic mice (APP and APP/PTau) and wild-type mice were treated for 4 weeks with the following compounds:

clioquinol 30 mg/kg p.o., clioquinol 10 mg/kg i.p., and compounds 11, T, 21, at 10 mg/kg, i.p. (or the vehicle used to dissolve the drugs for administration p.o. or i.p). 24 hours after the last drug administration, animals were killed and the brain and heart, spleen, kidney and testis dissected out. One of the brain hemispheres was frozen on dry ice, and the other hemisphere was placed in 4% paraformaldehyde. Sections of the latter were cut and stained to reveal the distribution of amyloid plaques using the Campbell-Switzer silver staining method (analysis of the tissue courtesy of NSA Laboratories, USA).

For therapeutic targeting of amyloidic pathways in neurodegenerative disease states such as AD an effect on plaque load in treated mouse models may be an indicator of therapeutic effect. In this context chronic administration of the new substituted phosphonates on β-amyloid plaques in two mouse models of Alzheimer's disease, the APP and APP/Tau transgenic mice, was investigated (FIG. 19). The chronic treatment did not reveal any overt signs of systemic toxicity or behavioural alterations in the treated animals, throughout the treatment, confirming thus the safety of the selected substituted phosphonates compounds at the dose chosen and using this regime of administration. In the APP transgenic mouse, there were significant amyloid plaques (large aggregates and also diffuse, punctate deposits) in the animals treated with vehicle only (p.o. or i.p.). Treatment with clioquinol led to apparent decreased plaque load, and especially a reduced load of large aggregates and a similar pattern was seen in the tissue from animals treated with the compound T while compounds 11 and 21 also reduced the plaque load.

The invention claimed is:

1. A method of decreasing amyloid aggregates comprising contacting the amyloid aggregates with a compound of formula Ib,

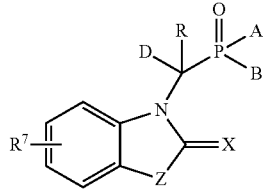

Ib wherein:

Z is O, S or $NR^1$;

X is O, S or $NR^1$;

$R^1$ is a hydrogen, a linear or branched $C_{1-40}$ alkyl, $C_{2-40}$ alkenyl, $C_{2-40}$ alkynyl, aryl, heteroaryl, $C_{1-40}$ alkylaryl or alkylheteroaryl;

R is hydrogen or a substituted or unsubstituted linear or branched $C_{1-40}$ alkyl, aryl or heteroaryl;

$R^7$ represents one or more ring substituents chosen from a hydrogen, a halide, a linear or branched $C_{1-40}$ alkyl, a $C_{2-40}$ alkenyl, a $C_{2-40}$ alkynyl, an aryl, a heteroaryl, a $C_{1-40}$ alkylaryl or alkylheteroaryl, a nitrile, a sulphonic acid or salt of sulphonic acid, a carboxy, an oxo, a carboxyalkyl, a carboxyalkoxy, a carboxyalkylamino, a carboxyalkylthio, an amide, a sulphonamide, a $C_{1-6}$ alkylalkoxy, $C_{1-6}$ alkylamino, $OR^2$, $SR^2$, $NR^3$, and $R^4$;

A and B are each, independently, $OR^2$, $SR^2$, $NR^3$, or $R^4$;

$R^2$, $R^3$ and $R^4$ are each, independently, hydrogen, a linear or branched $C_{1-40}$ alkyl, $C_{2-40}$ alkenyl, $C_{2-40}$ alkynyl, $C_{1-40}$ alkylaryl, or optionally a complex metal ion $M^{n+}/n$ wherein n is an integer from 1 to 8, or a linear or branched $C_{1-40}$ $NR^5R^6$ terminated alkyl chain;

D is hydrogen, a linear or branched $C_{1-40}$ alkyl, $C_{2-40}$ alkenyl, $C_{2-40}$ alkynyl, an aryl, a heteroaryl or $C_{1-40}$ alkylaryl or alkylheteroaryl or a linear or branched $C_{1-40}$ alkyl $NR^5R^6$ chain or a linear or branched $C_{1-40}$ mono or di alkyl ester or dialkyl ester $C_{1-40}$ alkylphosphonate or a linear or branched $C_{1-40}$ alkylphosphonic acid; and $R^5$ and $R^6$ are each, independently, hydrogen or a linear or branched $C_{1-40}$ alkyl.

2. A method of treating a subject having a disease characterized by amyloid deposition comprising administering to the subject a compound of formula Ib,

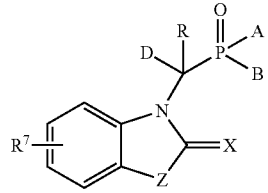

Ib wherein:

Z is O, S or $NR^1$;

X is O, S or $NR^1$;

$R^1$ is a hydrogen, a linear or branched $C_{1-40}$ alkyl, $C_{2-40}$ alkenyl, $C_{2-40}$ alkynyl, aryl, heteroaryl, $C_{1-40}$ alkylaryl or alkylheteroaryl;

R is hydrogen or a substituted or unsubstituted linear or branched $C_{1-40}$ alkyl, aryl or heteroaryl;

$R^7$ represents one or more ring substituents chosen from a hydrogen, a halide, a linear or branched $C_{1-40}$ alkyl, a $C_{2-40}$ alkenyl, a $C_{2-40}$ alkynyl, an aryl, a heteroaryl, a $C_{1-40}$ alkylaryl or alkylheteroaryl, a nitrile, a sulphonic acid or salt of sulphonic acid, a carboxy, an oxo, a carboxyalkyl, a carboxyalkoxy, a carboxyalkylamino, a carboxyalkylthio, an amide, a sulphonamide, a $C_{1-6}$ alkylalkoxy, $C_{1-6}$ alkylamino, $OR^2$, $SR^2$, $NR^3$, and $R^4$;

A and B are each, independently, $OR^2$, $SR^2$, $NR^3$, or $R^4$;

$R^2$, $R^3$ and $R^4$ are each, independently, hydrogen, a linear or branched $C_{1-40}$ alkyl, $C_{2-40}$ alkenyl, $C_{2-40}$ alkynyl, $C_{1-40}$ alkylaryl, or optionally a complex metal ion $M^{n+}/n$ wherein n is an integer from 1 to 8, or a linear or branched $C_{1-40}$ $NR^5R^6$ terminated alkyl chain;

D is hydrogen, a linear or branched $C_{1-40}$ alkyl, $C_{2-40}$ alkenyl, $C_{2-40}$ alkynyl, an aryl, a heteroaryl or $C_{1-40}$ alkylayl or alkylheteroaryl or a linear or branched $C_{1-40}$ alkyl $NR^5R^6$ chain or a linear or branched $C_{1-40}$ mono or di alkyl ester or dialkyl ester $C_{1-40}$ alkylphosphonate or a linear or branched $C_{1-40}$ alkylphosphonic acid; and $R^5$ and $R^6$ are each, independently, hydrogen or a linear or branched $C_{1-40}$ alkyl.

3. The method as claimed in claim 2, wherein the disease is Alzheimer's disease.

4. The method as claimed in claim 1, where in the compound is chosen from compound 8 or compound 10 as follows
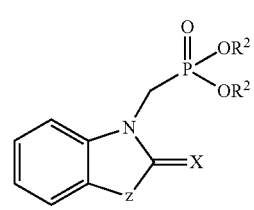
Compound 8
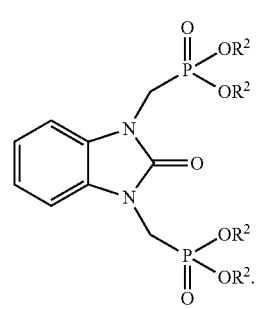
Compound 10
5. The method as claimed in claim 2, wherein the compound is chosen from compound 8 or compound 10 as follows
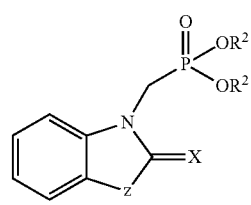
Compound 8
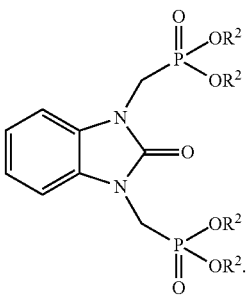
Compound 10
* * * * *